US012773424B2

(12) United States Patent
Rafaeli et al.

(10) Patent No.: US 12,773,424 B2
(45) Date of Patent: *Oct. 27, 2026

(54) METERED DOSE FOR DEMODEX AND DISORDERS RELATED THERETO

(71) Applicant: Azura Ophthalmics Ltd., Tel Aviv (IL)

(72) Inventors: Omer Rafaeli, Udim (IL); Charles Bosworth, Las Vegas, NV (US); Marc Gleeson, Longueville (AU); Yair Alster, Tel Aviv (IL); Hadas Rapaport, Zofar (IL)

(73) Assignee: Azura Ophthalmics Ltd., Tel Aviv (IL)

( * ) Notice: Subject to any disclaimer, the term of this patent is extended or adjusted under 35 U.S.C. 154(b) by 459 days.

This patent is subject to a terminal disclaimer.

(21) Appl. No.: 17/734,900

(22) Filed: May 2, 2022

(65) Prior Publication Data

US 2022/0323487 A1 Oct. 13, 2022

Related U.S. Application Data

(63) Continuation of application No. PCT/IB2020/000907, filed on Nov. 3, 2020.

(60) Provisional application No. 62/930,491, filed on Nov. 4, 2019.

(51) Int. Cl.

| | |
|---|---|
| ***A61K 33/04*** | (2006.01) |
| ***A61K 9/00*** | (2006.01) |
| ***A61K 9/06*** | (2006.01) |
| ***A61K 47/06*** | (2006.01) |
| ***A61K 47/38*** | (2006.01) |
| ***A61P 33/14*** | (2006.01) |

(52) U.S. Cl.

CPC ............ *A61K 33/04* (2013.01); *A61K 9/0048* (2013.01); *A61K 9/06* (2013.01); *A61K 47/06* (2013.01); *A61K 47/38* (2013.01); *A61P 33/14* (2018.01)

(58) Field of Classification Search

None

See application file for complete search history.

(56) References Cited

U.S. PATENT DOCUMENTS

2009/0061025 A1* 3/2009 Gao ......................... A61K 9/00 514/456
2016/0106775 A1 4/2016 Alster et al.
2017/0035785 A1 2/2017 Alster et al.
(Continued)

FOREIGN PATENT DOCUMENTS

WO WO-2017178892 A2 10/2017
WO WO-2021090058 A2 5/2021
WO WO-2021090070 A2 5/2021

OTHER PUBLICATIONS

Charles et al.. "Demodex Folliculorum and Blepharitis", archives of dermatology, vol. 88, issue 3, pp. 298-302, Sep. 1963. (Year: 1963).*

(Continued)

*Primary Examiner* — Kyung S Chang
(74) *Attorney, Agent, or Firm* — Faegre Drinker Biddle & Reath LLP

(57) ABSTRACT

Provided herein are pharmaceutical compositions and methods treating Demodex or a disorder thereof around the eye by application of a metered dose of a semi-solid product from a product tube.

14 Claims, 3 Drawing Sheets

(56) References Cited

U.S. PATENT DOCUMENTS

| | | | |
|---|---|---|---|
| 2017/0087179 | A1 | 3/2017 | Amselem et al. |
| 2022/0305052 | A1 | 9/2022 | Alster et al. |

OTHER PUBLICATIONS

NIH National Eye Institute, "Stargardt Disease", Dec. 4, 2024, pp. 1-4. (Year: 2024).*
Santvliet et al., "Determinants of eye drop size", Survey of Ophthalmology, vol. 49, issue 2, 2004, pp. 197-213. (Year: 2004).*
Bahn. The treatment of seborrheic blepharitis. South Med 47(8):749-53 (1954).
Berge et al. Pharmaceutical Salts. Journal of Pharmaceutical Sciences 66(1):1-19 (Jan. 1977).
Gonzalez-Hinojosa et al. Demodex and Rosacea: Is there a relationship? Ind. J Ophthalmol. 66(1):36-38 (2018).
Lavyel. Selsunef ointment to treat squamous blepharitis. Am J Ophthalmol 49:820-821 (1960).
PCT/IB2020/000907 International Invitation to Pay Additional Fees dated May 5, 2021.
PCT/IB2020/00907 International Search Report and Written Opinion dated Jul. 21, 2021.
PCT/IB2020/00980 International Search Report and Written Opinion dated May 12, 2021.
Post et al. Demodex Folliculorum and Blepharitis Arch. Dermatol. 88(3):298-302 (1963).
Rosenkrantz. Practical Applications of Topical Therapy for Allergic, Infectious, and Seborrheic Disorders. Clin. Tech. Small Anim. Pract. 21(3):106-116 (2006).
Rosenthal et al. effect of selenium sulfide on rabbit eyes. South Med J 55:318 (1962).
Schaumberg et al. The International Workshop on Meibomian Gland Dysfunction: Report of the Subcommittee on the Epidemiology Of, and Associated Risk Factors For, MGD. Invest. Ophthalmol. Vis. Sci. 52(4):1994-2005 (2011).
Thygeson et al. Seborrheic blepharitis. Trans Am Ophthalmol Soc. 52:173-88 (1954-1955).
Wong et al. Selenium (Selsun) in the Treatment of Marginal Blepharitis. AMA Arch Ophthalmol 55(2):246-253 (1956).
Cohen et al. Use of selsun in blepharitis marginalis. Am J Ophthalmol 38(4):560-562 (1954).
Deardorff. Chapter 86: Ophthalmic Preparations. Remington's Pharmaceutical Sciences (Osol A (Ed). pp. 1498-1517 (1980).

* cited by examiner

METERED DOSE FOR DEMODEX AND DISORDERS RELATED THERETO

CROSS-REFERENCE TO RELATED APPLICATIONS

This application is a continuation of International Application No. PCT/IB2020/000907, filed internationally on Nov. 3, 2020, which claims the benefit of U.S. Provisional Application No. 62/930,491, filed on Nov. 4, 2019, all of which are hereby incorporated by reference in their entireties.

BACKGROUND OF THE INVENTION

The Demodex mite is an ectoparasite that can reside in hair follicles and sebaceous glands. Demodex mites can infest the eyelids, eyelashes, and glands of surrounding ocular tissue (e.g., meibomian glands). Demodex can cause blepharitis (e.g., anterior blepharitis, posterior blepharitis, ocular rosacea, blepharoconjunctivitis). Blepharitis is a common inflammation of the eye affecting the eyelashes, eyelids, and ocular surface.

Clinical studies of topical ocular formulations of selenium disulfide have been completed in seborrheic blepharitis. In one, selenium disulfide 0.5% applied twice-weekly for 2 weeks followed by once-weekly administration for 1 month and then 1 or 2 times a month administration for 6-10 months in 100 subjects. Bahn GC. The treatment of seborrheic blepharitis. *South Med* J. 1954 August; 47(8):749-53. In a second, the use of Selsunef 0.5% ($SeS_2$) Ointment (Abbott), in the clinic, where gentled and controlled application was performed by the physician that was also removed the ointment after 30 min by a cotton wool. Lavyel A. Selsunef Ointment to Treat Squamous Blepharitis. AJO 1960. Great care was always taken not to introduce any of the ointment into the conjunctival sac. In one case, where the patient administered Selsunef himself, contrary to medical advice, severe keratitis promptly developed. One patient (1%) inadvertently put the drug into her conjunctival sac and developed moderately severe conjunctivitis which subsided with discontinuation of the drug. In another, selenium disulfide 0.5% was applied twice-weekly for a period of between 2 months to 1 year in 89 seborrheic blepharitis patients. Thygeson P, et al. Seborrheic blepharitis. *Trans Am Ophthalmol Soc.* 1954-1955; 52:173-88. Epithelial keratitis occurred in 6 cases. In 4 of these the keratitis was transient but in 2 it persisted for a matter of days, and in 1 for as long as a week. In another, selenium disulfide 0.5% vs ammoniated mercury (control) was applied twice-daily (BID) for 4 weeks in combination with daily eyelid cleaning in 76 seborrheic blepharitis eyes. Wong AS, et al. Selenium (selsun) in the treatment of marginal blepharitis. *AMA Arch Ophthalmol.* 1956 February; 55(2):246-53. Two patients experienced keratitis, conjunctivitis with erythematous and swollen lids. Across these studies topical ocular application of selenium disulfide up to maximal daily exposure of 0.5% BID was associated with self-limiting keratitis which resolved upon cessation of treatment.

As Dr. Ralph O Rychener noted in the discussion at the end of Thygeson and Vaughan's (1954) paper, "While selenium sulfide [disulfide] solution first became available, I asked the Abbott Company to make up some ointment for use on the lids. They furnished 0.5 percent ointment which proved to be too strong, because all of our patients complained so bitterly of the burning of the conjunctiva that they refused to carry on the treatment at home." Thus, it was expected that a dose above and potentially including 0.5% selenium disulfide would not be well tolerated in clinical practice. In these studies patients were only using concentrations of up to 0.5% because there was animal data suggesting that higher concentration can be toxic to the ocular surface. The animal studies performed in rabbit have indicated that concentration higher than 0.5% would be toxic to the cornea. The effect of 0.5% and 2.5% $SeS_2$ on rabbits corneas and conjunctivas was evaluated and it was found that the use of 0.5% in 54 Rabbits eyes was safe, while the use of 2.5% $SeS_2$ in 14 Rabbits eyes exhibited chemosis, redness, corneal clouding, corneal edema, corneal staining and corrosive ulcers within 2 hours after application. Rosenthal J W, et al. effect of selenium sulfide on rabbit eyes. *Southern medical journal* 1962. The treatment was used to treat seborrheic blepharitis (seborrhea of the skin of the eye lid margin) and while scalp seborrheic dermatitis was treated with 2.5% of $SeS_2$, based on data from the human studies and animal experiments a maximal concentration of 0.5% was advocated to provide potential benefit. These studies were also limiting the dosing frequency and duration of treatment to avoid such side effects. Furthermore, patients were instructed to use it cautiously and apply it over the outer lid only carefully so it does not come in contact with the ocular surface. Patients were also instructed in some studies to wash their eyes after the application. Post C. Demodex Folliculorum and Blepharitis. *ArchDerm* 1963.

A treatment for Demodex that reduces infestation and does not cause toxic side effects is desirable.

SUMMARY OF THE INVENTION

While a commonly used agent for Demodex is tea tree oil, it, as well as other therapies for Demodex, can cause dermatitis, allergy, and ocular irritation, especially at higher concentrations. In some instances, Demodex associated with blepharatis is treated with an ointment comprising selenium disulfide 0.5% and hydrocortisone acetate 0.5%. However, across the investigations with such ointment, physician and patient topical ocular application of $SeS_2$, up to a maximal daily exposure of 0.5% BID is associated with self-limiting side effects (e.g., keratitis). Such side-effects have limited the use of $SeS_2$ as a treatment option. Moreover, in some instances, selenium containing shampoos, or dilutions thereof, are considered for the treatment (killing) of Demodex. Such uses are not useful in or around the eye, however, because the presence of surfactants leads to undesirable effects, such as irritation of the eye. Therefore, the development of a safe formulation for the treatment of Demodex, or related diseases and disorders, such as that can be self-administered is needed.

Provided in certain embodiments, are methods and compositions for treating Demodex and related disorders. Further, in some instances herein, such compounds, methods and formulations are useful in providing such therapeutic benefits are achieved while limiting or eliminating self-limiting side effects (e.g., keratitis), such as is often observed in therapies involving therapeutic agents described herein. In some instances, such therapies provided herein result in improved therapeutic efficacy, such as based, at least in part, on improved patient compliance.

In some embodiments, provided herein are methods of treating Demodex (e.g., infestation thereof) in or around the eye (e.g., on the eyelid, such as on or around the eyelashes), such as by administering a composition in or around the eye (e.g., to the eyelid, such as eyelid margin) of an individual (e.g., in need thereof). In certain embodiments, the method is a method of killing or otherwise reducing the amount (or killing) of Demodex in or around the eye. In some embodiments, the method is a method of repelling or otherwise inhibiting an increase in population (or repelling) of Demodex in or around the eye. In some embodiments, the method is a method of reducing the likelihood or risk of having an infestation of Demodex. In certain embodiments, an individual susceptible or suspected of being susceptible of having an infestation of Demodex.

In certain embodiments, provided herein is a method for treating Demodex or disorder thereof in or around the eye, such as in an individual in need thereof. In some embodiments, the method comprises administering a therapeutically effective amount of a pharmaceutical composition to an ocular surface, surrounding ocular tissues, or a combination thereof of the individual. In certain embodiments, the pharmaceutical composition comprises selenium disulfide ($SeS_2$), e.g., in a therapeutically effective amount and/or therapeutically effective concentration, such as described herein. In specific embodiments, the pharmaceutical composition comprises selenium disulfide ($SeS_2$) in a therapeutically effective amount and a therapeutically effective concentration. In some embodiments, the therapeutically effective concentration of selenium disulfide ($SeS_2$) in the pharmaceutical composition is about 0.05 wt. % to about 3 wt. %. In specific embodiments, the therapeutically effective concentration of selenium disulfide ($SeS_2$) in the pharmaceutical composition is about 0.1 wt. % to about 2.5 wt. % of $SeS_2$. In other specific embodiments, the therapeutically effective concentration of selenium disulfide ($SeS_2$) in the pharmaceutical composition is about 0.05 wt. % to about 1 wt. %. In some embodiments, the pharmaceutical composition is administered to the individual (e.g., in a manner described herein) in a volume of about 25 microliters (μL) or less. In specific embodiments, the volume is less than 25 μL. In more specific embodiments, the pharmaceutical composition is administered to the individual (e.g., in a manner described herein) in a volume of about 5 microliters (μL) to less than 25 μL. In specific embodiments, the pharmaceutical composition is administered to the individual (e.g., in a manner described herein) in a volume of about 0.1 microliters (μL) to less than 25 microliters (μL). In some specific embodiments, the volume administered is 3 microliters (μL) to less than 25 μL. In certain specific embodiments, the volume administered is low, such as about 0.1 microliters (μL) to about 5 microliters (μL), such as about 0.2 microliters (μL) to about 3 microliters (μL). In some embodiments, the volume administered is about 10 μL or less (e.g., about 3 μL to about 10 μL). In specific embodiments, the volume administered is about 5 μL. In some embodiments, the volume administered is about 0.3 microliters (μL) to about 0.5 microliters (μL). In specific embodiments, the volume administered is about 0.3 microliters. In certain embodiments, the volume administered is about 0.3 μL to about 20 μL.

In an aspect, provided herein is a method for treating Demodex (e.g., infestation thereof) in or around the eye in an individual in need thereof, the method comprising administering a therapeutically effective amount of a pharmaceutical composition to an ocular surface, surrounding ocular tissues, or a combination thereof of the individual. In some embodiments, the pharmaceutical composition comprising a therapeutically effective amount of selenium disulfide ($SeS_2$) to reduce the population of Demodex and/or inhibit the overgrowth of Demodex. In some embodiments, the pharmaceutical composition comprising the therapeutically effective amount of $SeS_2$ in a therapeutically effective concentration, the therapeutically effective concentration being at least 0.01 wt. % (e.g., about 0.01 wt. % to about 10 wt. %, such as, about 0.01 wt. % to about 2.5 wt. %, about 0.02 wt. % to less than about 1.5 wt. %, or about 0.05 wt. % to about 1 wt. 00 such as to inhibit the overgrowth of (or repel) Demodex)_(e.g., about 0.1 wt. % to about 20 wt. 00 such as about 0.5 to about 20 wt. %, or about 2.5 wt. % to about 20 wt. %, or greater than about 5 wt. %, such as to reduce the population of (or kill) Demodex) of $SeS_2$; and the pharmaceutical composition being administered in a volume of about 25 microliters (μL) or less (e.g., less than 25 μL or other volume provided herein).

In some embodiments, a method provided herein comprises administration of a pharmaceutical composition and a second pharmaceutical composition (e.g., subsequent to the administration of the first concentration, such as at least one day later). In certain embodiments, the first composition is a high concentration (e.g., about 2.5 wt. % to about 20 wt. %, such as about 2.5 wt. % to about 5 wt. % selenium disulfide) and the second composition is a inhibiting (or repelling) concentration (e.g., about 0.01 wt. % to about 2.5 wt. %, such as about 0.1 wt. % to about 2.5 wt. % selenium disulfide).

In some embodiments, a method provided herein comprises administering the pharmaceutical composition in an amount or volume sufficient to (a) provide a therapeutic benefit, while also (b) reducing side effects to a tolerable level (e.g., a level wherein patient compliance is increased, such as relative to otherwise similar treatments having a different active concentration or active concentration and composition volume). In some embodiments, the pharmaceutical composition is administered to the individual (e.g., in a manner described herein) in a volume of about 25 microliters (μL) or less (e.g., less than 25 μL). In specific embodiments, the pharmaceutical composition is administered to the individual (e.g., in a manner described herein) in a volume of about 0.1 microliters (μL) to less than 25 microliters (μL). In some specific embodiments, the volume administered is 3 microliters (μL) to about 25 microliters (μL) (e.g., less than 25 μL). In certain specific embodiments, the volume administered is low, such as about 0.1 microliters (μL) to about 5 microliters (μL), such as about 0.2 microliters (μL) to about 3 microliters (μL). In some embodiments, the volume administered is about 10 μL or less (e.g., about 3 μL to about 10 μL). In specific embodiments, the volume administered is about 5 μL. In some embodiments, the volume administered is about 0.3 microliters (μL) to about 0.5 microliters (μL). In specific embodiments, the volume administered is about 0.3 microliters In certain embodiments, the pharmaceutical composition and/or method of administering the same does not cause substantial keratitis, keratoconjunctivitis, or a combination thereof.

In some embodiments, a method provided herein comprises administering the pharmaceutical composition in a concentration sufficient to (a) provide a therapeutic benefit, while also (b) reducing side effects to a tolerable level (e.g., a level wherein patient compliance is increased, such as relative to otherwise similar treatments having a different active concentration or active concentration and composition volume), particularly when administered in a composition having an amount or volume described herein. In certain instances, it is unexpectedly shown, such as in the examples herein, that compositions comprising selenium disulfide ($SeS_2$), even in high concentrations (e.g., greater than 0.5 wt. %), are well tolerated in therapeutic applications, such as when administered in a sufficiently small volume (e.g., less than 25 μL). In some embodiments, the therapeutically effective concentration of selenium disulfide ($SeS_2$) in the pharmaceutical composition is about 0.05 wt. % to about 3 wt. % (e.g., about 0.1 wt. % to about 3 wt. %, at least 0.5 wt. % to about 3 wt. %, about 0.75 wt. % to about 3 wt. %). In specific embodiments, the therapeutically effective concentration of selenium disulfide ($SeS_2$) in the pharmaceutical composition is about 0.1 wt. % to about 2.5 wt. % of $SeS_2$. In certain embodiments, the therapeutically effective concentration comprises about 0.5 wt. % to about 1.0 wt. % $SeS_2$ (e.g., about 0.1 wt. % to about 2.5 wt. %, at least 0.5 wt. % to about 2.5 wt. %, about 0.75 wt. % to about 2.5 wt. %).

In certain embodiments, the therapeutically effective amount of $SeS_2$ is tied to the concentration and volume administered. In various embodiments, the therapeutically effective amount of $SeS_2$ is any suitable amount, such as about 1 mg to about 10 mg, such as about 2 mg to about 8 mg, such as about 3 mg to about 6 mg, or about 4 mg.

In various embodiments provided herein, the pharmaceutical composition is in any suitable form or formulation. In some embodiments, the pharmaceutical composition is formulated as a semi-solid. In certain embodiments, the pharmaceutical composition is an ointment. In various embodiments, the ointment comprises any suitable carrier or other excipient. In some embodiments, an ointment provided herein petrolatum. In certain embodiments, the pharmaceutical composition is a cream, gel, or lotion. In some embodiments, the pharmaceutical composition is a solution, suspension, or emulsion. In certain embodiments, the pharmaceutical composition comprises nanoparticles, microparticles, and/or liposomes (e.g., in a suspension).

In certain embodiments, a composition provided or otherwise described herein is administered, such as in the amount or volume described herein, in any suitable manner and/or utilizing any suitable device or applicator. In specific embodiments, the pharmaceutical composition is provided using a device, such as a device configured to deliver volume of about 25 μL or less (e.g., preferably, less than 25 μL). In more specific embodiments, the device is configured to deliver a volume described as being administered according to the disclosures provided herein. In certain embodiments, the pharmaceutical composition is administered directly, such as utilizing a device or applicator thereof, to an ocular surface, surrounding ocular tissues, or a combination thereof. In alternative embodiments, the pharmaceutical composition is administered, such as utilizing the device, to a finger, after which the pharmaceutical composition is administered (e.g., via finger) to an ocular surface, surrounding ocular tissues, or a combination thereof.

In certain embodiments, the device, or applicator thereof, is configured to administer an effective volume. In some embodiments, such as wherein the device, or applicator thereof, administers the effective volume directly to the desired area, the device, or applicator thereof, delivers a volume of pharmaceutical composition consistent with the volume of pharmaceutical composition described in the various embodiments of methods provided herein. In specific embodiments, the device, or applicator thereof, delivers a volume of about 25 μL or less (e.g., preferably, less than 25 μL), such as about 0.10.1 microliters (μL) to less than 25 μL (e.g., about 5 μL to less than 25 μL), such as about 0.3 microliters (μL) to about 20 μL. In specific embodiments, the volume is about 3 microliters (μL) to less than 25 μL. In some embodiments, the volume is about 10 μL or less (e.g., about 3 μL to about 10 μL). In specific embodiments, the volume is about 5 μL. In some embodiments, such as wherein deliver is to a finger of the individual, the finger of a medical provider, or an applicator (e.g., that is not a part of the device), slight overage volumes (e.g., up to 50%, up to 30%, up to 20%, up to 10%, or the like) are provided and/or delivered by the device, such as to facilitate delivery of the indicated amount to the indicated location.

In some embodiments, the pharmaceutical composition is administered to any suitable surface, such as consistent with the descriptions provided herein. In specific embodiments, the pharmaceutical composition is administered to an eyelid of the individual, an eyelash of the individual, or a combination thereof. In some embodiments, the pharmaceutical composition is administered (e.g., directly to) or delivered to an eyelid margin of the eyelid.

In various embodiments, any suitable individual administers the pharmaceutical composition to the indicated or desired location. In some embodiments, the pharmaceutical composition is administered by the individual receiving treatment of the pharmaceutical composition. In other embodiments, the pharmaceutical composition is administered by a medical provider.

In certain embodiments, the disease or disorder in or around the eye is or is caused by Demodex mites (e.g., Demodex *brevis*, Demodex folicularum, etc.). In some embodiments, the Demodex mites cause a disease or disorder in or around the eye that is associated with blepharitis. In some embodiments, the blepharitis is, for example, anterior blepharitis, posterior blepharitis, ocular rosacea, blepharoconjunctivitis, or any combination thereof.

In certain embodiments, a method of treatment provided herein is for the treatment of any suitable disease or disorder in or around the eye associated with Demodex, such as a disease or disorder in or around the eye associated with Demodex responsive to such treatment. In some embodiments, the disease or disorder in or around the eye is or is caused by Demodex mites. In some embodiments, the disease or disorder in or around the eye is associated with blepharitis, hyperkeratosis, keratoconjunctivitis, or any combination thereof.

In certain embodiments, a method of treatment provided herein comprises administration of the pharmaceutical composition, e.g., in the manner described, a plurality of times. In some embodiments, such plurality of administrations are administered on a predetermined schedule, such as once daily, twice daily, at least thrice daily, every other day, ever third day, weekly, or the like.

In some embodiments, provided herein is a method for treating Demodex or disorder thereof in or around the eye of an individual in need thereof, the method comprising administering in a dosing regimen a therapeutically effective amount of a pharmaceutical composition to an ocular surface, surrounding ocular tissues, or a combination thereof of the individual; the pharmaceutical composition comprising a therapeutically effective amount of selenium disulfide ($SeS_2$); the pharmaceutical composition comprising the therapeutically effective amount of $SeS_2$ in a therapeutically effective concentration, the therapeutically effective concentration being about 0.1 wt. % to about 2.5 wt. %; and during each administration of the dosing regimen, the pharmaceutical composition being administered in a volume of about 25 microliters (μL) or less (e.g., preferably, less than 25 μL).

In certain embodiments, a dosing regimen of any method provided herein comprises administration of the pharmaceutical composition at least a first time and at least a second time (e.g., in a volume as set forth herein during both the first and the second administrations). In some embodiments, the second time is subsequent to at least the first time, such as by at least 6 hours, at least 12 hours, at least 24 hours, or more. In some embodiments, the dosing regimen comprises administration of the pharmaceutical composition at least once-weekly for at least two administrations (e.g., at least 3 administration, at least 4 administration, or more). In certain embodiments, the dosing regimen is twice-weekly. In some embodiments, the dosing regimen is once-daily.

In certain embodiments, provided herein is a method for treating bacterial infection in collarettes of an individual in need thereof. In specific embodiments, the method comprises administering a therapeutically effective amount of selenium disulfide ($SeS_2$) to bacterial infected collarettes of the individual. Administration of such actives are in any suitable manner or regimen, such as described in the various methods provided herein.

In some embodiments, the collarettes are present on or around one or more eyelash(es) of the individual. In some embodiments, the collarettes comprise one or more live and/or dead Demodex. In certain embodiments, the bacteria of the bacterial infected collarettes are in a space between live and/or dead Demodex and an eyelash.

In certain embodiments, the therapeutically effective amount of $SeS_2$ is administered in a pharmaceutical composition comprising a therapeutically effective concentration of the $SeS_2$, the therapeutically effective concentration being about 0.1 wt. % to about 2.5 wt. % of $SeS_2$; and the pharmaceutical composition being administered in a volume of less than 25 microliters (μL). In some embodiments, the therapeutically effective concentration comprises about 0.5 wt. % to about 1.0 wt. % $SeS_2$ or other concentration provided in any methods described herein. In some embodiments, the volume administered is about 10 μL or less (or any other volume of a method described herein). In specific embodiments, the volume administered is about 5 μL. In some embodiments, the selenium disulfide is administered in a therapeutically effective amount, such as about 4 mg (or any other amount described in a method herein).

In some embodiments, the selenium disulfide is administered in any suitable pharmaceutical composition, such as in the form of a semi-solid. In specific embodiments, the pharmaceutical composition is an ointment. In certain embodiments, the pharmaceutical composition is a cream, gel, or lotion. In some embodiments, the pharmaceutical composition is a solution, suspension, or emulsion. In certain embodiments, the pharmaceutical composition comprises nanoparticles, microparticles, and/or liposomes (e.g., in a suspension).

In certain embodiments, a composition provided or otherwise described herein is administered, such as in the amount or volume described herein, in any suitable manner and/or utilizing any suitable device or applicator. In specific embodiments, the pharmaceutical composition is provided using a device, such as a device configured to deliver volume of about 25 μL or less (e.g., preferably, less than 25 μL). In more specific embodiments, the device is configured to deliver a volume described as being administered according to the disclosures provided herein. In certain embodiments, the pharmaceutical composition is administered directly, such as utilizing a device or applicator thereof, to an ocular surface, surrounding ocular tissues, or a combination thereof. In alternative embodiments, the pharmaceutical composition is administered, such as utilizing the device, to a finger, after which the pharmaceutical composition is administered (e.g., via finger) to an ocular surface, surrounding ocular tissues, or a combination thereof.

In certain embodiments, the device, or applicator thereof, is configured to administer an effective volume. In some embodiments, such as wherein the device, or applicator thereof, administers the effective volume directly to the desired area, the device, or applicator thereof, delivers a volume of pharmaceutical composition consistent with the volume of pharmaceutical composition described in the various embodiments of methods provided herein. In specific embodiments, the device, or applicator thereof, delivers a volume of about 25 μL or less (e.g., preferably, less than 25 μL), such as about 0.1 μL to less than 25 μL (e.g., about 5 microliters (μL) to less than 25 μL). In specific embodiments, the device, or applicator thereof, delivers a volume of about 0.3 μL to about 20 μL. In specific embodiments, the volume is about 3 microliters (μL) to less than 25 μL. In some embodiments, the volume is about 10 μL or less (e.g., about 3 μL to about 10 μL). In specific embodiments, the volume is about 5 μL. In some embodiments, such as wherein deliver is to a finger of the individual, the finger of a medical provider, or an applicator (e.g., that is not a part of the device), slight overage volumes (e.g., up to 50%, up to 30%, up to 20%, up to 10%, or the like) are provided and/or delivered by the device, such as to facilitate delivery of the indicated amount to the indicated location.

In some embodiments, the pharmaceutical composition is administered to any suitable surface, such as consistent with the descriptions provided herein. In specific embodiments, the pharmaceutical composition is administered to an eyelid of the individual, an eyelash of the individual, or a combination thereof. In some embodiments, the pharmaceutical composition is administered (e.g., directly to) or delivered to an eyelid margin of the eyelid.

In various embodiments, any suitable individual administers the pharmaceutical composition to the indicated or desired location. In some embodiments, the pharmaceutical composition is administered by the individual receiving treatment of the pharmaceutical composition. In other embodiments, the pharmaceutical composition is administered by a medical provider.

Also provided in certain embodiments herein are pharmaceutical compositions. In some embodiments, provided herein is any pharmaceutical composition described in any method described herein. Similarly, in various embodiment provided herein, a method provided herein comprises administering any pharmaceutical composition provided herein. In certain embodiments, provided herein is a pharmaceutical composition comprising a therapeutically effective amount of selenium disulfide ($SeS_2$). In some embodiments, the pharmaceutical composition comprises the $SeS_2$ in a therapeutically effective concentration.

In some embodiments, a composition provided herein comprises an amount or volume sufficient to (a) provide a therapeutic benefit, while also (b) reducing side effects to a tolerable level (e.g., a level wherein patient compliance is increased, such as relative to otherwise similar treatments having a different active concentration or active concentration and composition volume). In some embodiments, the pharmaceutical composition has a volume (e.g., discrete volume, such as wherein the volume of the composition is discrete or separate from larger, bulk volume of a similar of about 25 microliters (μL) or less (e.g., preferably, less than 25 μL). In specific embodiments, the pharmaceutical composition has a (e.g., discrete) volume of about 0.1 μL to less than 25 μL about 3 microliters (μL) to less than 25 μL. In some embodiments, the (e.g., discrete) volume is about 10 μL or less (e.g., about 3 μL to about 10 μL). In specific embodiments, the (e.g., discrete) volume is about 5 μL. In some embodiments, the (e.g., discrete) volume is about is about 0.3 μL to about 20 μL.

In some embodiments, a composition provided herein comprises selenium disulfide in a concentration sufficient to (a) provide a therapeutic benefit, while also (b) reducing side effects to a tolerable level (e.g., a level wherein patient compliance is increased, such as relative to otherwise similar treatments having a different active concentration or active concentration and composition volume), particularly when the composition has an amount or volume described herein. In some embodiments, the therapeutically effective concentration of selenium disulfide ($SeS_2$) in the pharmaceutical composition is about 0.05 wt. % to about 3 wt. %. In specific embodiments, the therapeutically effective concentration of selenium disulfide ($SeS_2$) in the pharmaceutical composition is about 0.1 wt. % to about 2.5 wt. % of $SeS_2$. In certain embodiments, the therapeutically effective concentration comprises about 0.5 wt. % to about 1.0 wt. % $SeS_2$.

In certain embodiments, the amount of selenium disulfide ($SeS_2$) is tied to the concentration and volume administered. In various embodiments, the amount of $SeS_2$ is any suitable amount, such as about 1 microgram to about 10 mg, such as about 1 mg to about 10 mg, such as about 2 mg to about 8 mg, such as about 3 mg to about 6 mg, or about 4 mg.

In various embodiments provided herein, the pharmaceutical composition is in any suitable form or formulation. In some embodiments, the pharmaceutical composition is formulated as a semi-solid. In certain embodiments, the pharmaceutical composition is an ointment. In various embodiments, the ointment comprises any suitable carrier or other excipient. In some embodiments, an ointment provided herein petrolatum.

In certain embodiments, a composition provided or otherwise described herein is combined (e.g., in a kit) with any suitable device or applicator. In specific embodiments, the device is configured to deliver volume of about 25 μL or less (e.g., preferably, less than 25 μL). In more specific embodiments, the device is configured to deliver a volume described as being administered according to the disclosures provided herein. In certain embodiments, the pharmaceutical composition is administered directly, such as utilizing a device or applicator thereof, to an ocular surface, surrounding ocular tissues, or a combination thereof. In alternative embodiments, the pharmaceutical composition is administered, such as utilizing the device, to a finger, after which the pharmaceutical composition is administered (e.g., via finger) to an ocular surface, surrounding ocular tissues, or a combination thereof. In certain embodiments, the device, or applicator thereof, is configured to administer an effective volume. In some embodiments, such as wherein the device, or applicator thereof, administers the effective volume directly to the desired area, the device, or applicator thereof, delivers a volume of pharmaceutical composition consistent with the volume of pharmaceutical composition described in the various embodiments of methods provided herein. In specific embodiments, the device, or applicator thereof, delivers a volume of less than 25 μL, such as about 0.1 μL to less than 25 μL (e.g., 5 microliters (μL) to less than 25 μL).). In specific embodiments, the volume is about 3 microliters (μL) to less than 25 μL. In some embodiments, the volume is about 10 μL or less (e.g., about 3 μL to about 10 μL). In specific embodiments, the volume is about 5 μL. In some embodiments, such as wherein deliver is to a finger of the individual, the finger of a medical provider, or an applicator (e.g., that is not a part of the device), slight overage volumes (e.g., up to 50%, up to 30%, up to 20%, up to 10%, or the like) are provided and/or delivered by the device, such as to facilitate delivery of the indicated amount to the indicated location.

In some embodiments, the pharmaceutical composition is formulated for ophthalmic purposes and/or is ophthalmically safe. In certain embodiments, the pharmaceutical composition does not comprise a surfactant. In some embodiments, the pharmaceutical composition does not cause substantial keratitis.

Another aspect provided herein is a kit comprising: two or more product tubes containing a semi-solid product, each product tube having a semi-solid product; and a dispenser. In some embodiments, the kit further comprises at least one of an applicator, an instruction manual, a mirror, and a wipe.

BRIEF DESCRIPTION OF THE DRAWINGS

The novel features of the disclosure are set forth with particularity in the appended claims. A better understanding of the features and advantages of the present disclosure will be obtained by reference to the following detailed description that sets forth illustrative embodiments, in which the principles of the disclosure are utilized, and the accompanying drawings of which:

DETAILED DESCRIPTION OF THE INVENTION

Figure 1:
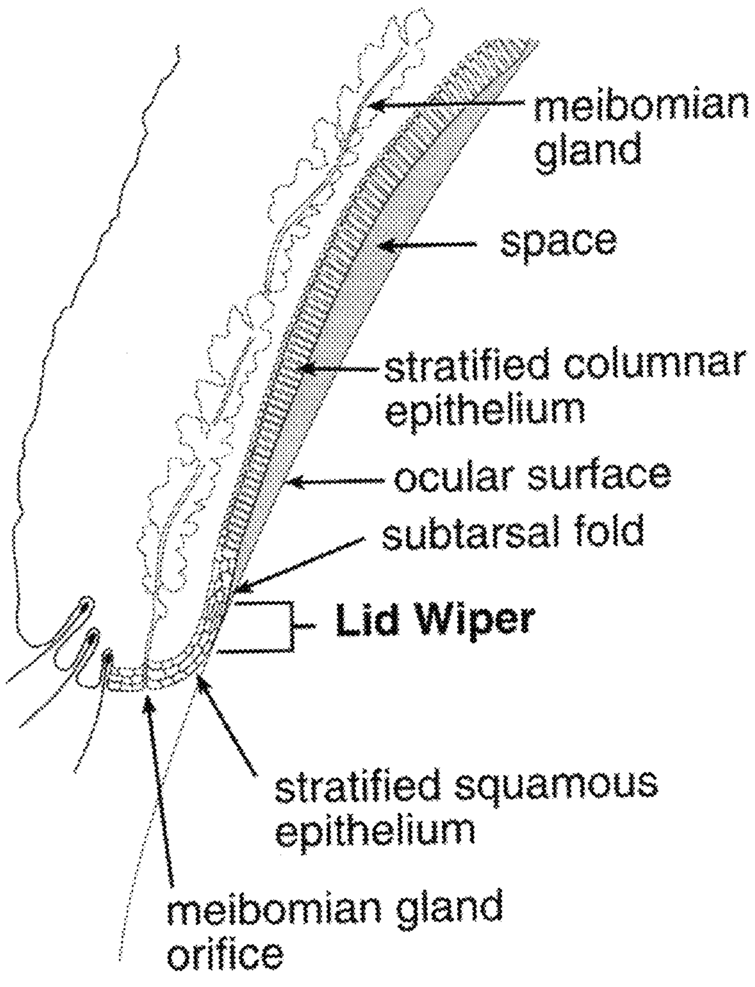
FIG. 1 illustrates a cross-sectional schematic of an exemplary normally functioning eyelid in relation to an ocular surface.

Described herein are pharmaceutical compositions and methods for treating Demodex and/or associated disorders, such as blepharitis associated with Demodex, by administering selenium disulfide to ocular surface, surrounding ocular tissues, or a combination thereof (e.g., to the eyelid, such as the eyelid margin). The agents described herein include agents for acute therapies, for use, e.g., by a physician or other trained specialist, and agents for chronic therapies, e.g., either by a physician or other trained specialist, or by the patient. In certain embodiments, provided herein are pharmaceutical compositions comprising therapeutically effective concentrations of selenium disulfide ($SeS_2$). In some embodiments, provided herein are pharmaceutical compositions comprising therapeutically effective amounts of selenium disulfide ($SeS_2$). In certain embodiments, provided herein are pharmaceutical compositions comprising therapeutically effective volumes (e.g., combined with a therapeutically effective concentration of selenium disulfide ($SeS_2$)). Also provided herein are methods of treatment, such as of (e.g., ocular) Demodex, comprising administering such a composition.

In certain instances, two types of Demodex mites are Demodex *Brevis* and the Demodex folicularum. In some instances, in ocular Demodex, Demodex folicularum are found in clusters around eyelashes and eyelid tissue and/or Demodex *brevis* resided in sebaceous and Meibomian glands. In some instances, adult mites are 0.2 millimeters (mm) to 0.4 mm long and have a semitransparent, elongated bodies. In certain instances, eight short, segmented legs are attached to the first body segment. In some instances, mites have pin-like mouthparts for eating skin cells and oils (sebum), which accumulate in the hair follicles or glands. The mites may leave the hair follicles and move at a speed of a few mm per hour.

In some instances, Demodex blepharitis is detected by the presence of Blepharitis and cylindrical dandruff at the base of the eyelashes, which is considered, in certain instances, as pathognomonic of Demodex infestation. In some instances, ocular Demodex or Demodicosis is diagnosed by epilating the eyelashes under light microscope. In some instances, several eyelashes from either or each of upper and lower eyelids are evaluated under microscope to determine ocular Demodex, such as by determining the presence and/or number of living mites. In other instances, ocular Demodex is identified with in situ slit microscope without eyelashes epilation.

InIn certain embodiments, treating Demodex provided herein comprising reducing the population (or killing), reducing the amount (or killing or repelling), or inhibiting overgrowth of a population of (or repelling) Demodex mites (e.g., Demodex *Brevis* or Demodex folicularum), such as by applying a composition provided herein.

In some embodiments, selenium disulfide-containing agents (e.g., selenium disulfide ($SeS_2$)) is used, e.g., in the treatment of Demodex, such as through restoration of meibomian glands. In some instances, such agents described herein reduce Demodex infestation, such as by disrupting the physiology of Demodex mites. In some embodiments, the selenium disulfide-containing agents (e.g., selenium disulfide ($SeS_2$)) inhibit the overgrowth of Demodex mite populations remove lipids, protein, and other debris from an ocular surface that Demodex mites consume.

In some embodiments, agents provided herein are administered in a method herein as an acute therapy (e.g., by a trained specialist, physician, or the patient) or as a chronic therapy (e.g., in the hands of a patient, or alternatively, by a trained specialist or physician).

In certain embodiments, any method provided herein comprises administration of an agent or composition described herein to the eyelid of an individual (e.g., an individual in need thereof).

In specific embodiments, administration of the agent and/or composition comprises topical administration of the agent or composition (in an amount and/or concentration as described herein) to the eyelid margin of the patient in need thereof. In some instances, the eyelid margin comprises the edge of the eyelid, such as in the area at and around the juncture of the conjunctiva and the skin and/or comprising the eyelashes and/or opening of the meibomian glands, such as illustrated in FIG. 1.

In some embodiments, the active agents are formulated and applied such that they are acceptable to the surface of the eye (i.e. not causing undue irritation or disruption to the epithelial surface of the eye), and do not compromise lipid producing cells in contact with the composition.

In some embodiments, the composition is applied for a duration and frequency that is acceptable and practical to the physician or patient administering the agent. For example, a physician applies a composition described herein weekly or twice a week for several weeks to induce increase in the quantity of lipids secreted from the meibomian gland and the patient applies a different composition on a daily basis, or the patient uses a more potent composition on a daily basis for several weeks and then, subsequently uses a less potent composition of a daily basis thereafter. In some embodiments, the composition is applied by the patient on a daily basis once or several times a day.

In some embodiments, the method of application varies, depending on the concentration of the agent and/or the extent of lipid deficiency and/or Demodex infestation. In other embodiments, the method of application of the composition is tailored to enhance the penetration or residency time on the target tissue in order to enhance the effect of the treatment. In other embodiments, the method of application of the composition is varied to enhance the penetration or residency time on the target tissue to minimize the amount of application time necessary. In other embodiments, the composition is formulated (e.g., by adjusting viscosity and/or skin-adhesiveness) to increase contact with the target tissue while minimizing contact with non-target tissues, including the eye, and thus limit or reduce any undesired collateral activity.

In certain embodiments, the concentration of the agent and of the excipients is optimized to deliver the minimum effective concentration of the agent to achieve the therapeutic benefit while minimizing any ocular irritation or disruption, or irritation or disruption to surrounding ocular tissues.

Described in some embodiments herein are compositions, such as useful for treating Demodex infestation. Said compositions comprise anhydrous selenium disulfide ($SeS_2$) wherein the $SeS_2$ is dispersed in an anhydrous vehicle in a non-aggregated manner, the dispersion of $SeS_2$ is stable physically and chemically without use of surfactants, suspending agents, or dispersing agents, and the composition does not contain an excipient and does not cause significant irritation.

In some instances, contacting $SeS_2$ with aqueous medium can cause immediate and spontaneous aggregation, such that $SeS_2$ particles with an average size of 5 to 10 microns will form large aggregates of 50 to 500 microns average size. In some instances, $SeS_2$ in marketed products (e.g., Sebosel™) is present in such aggregates. In certain instances, compositions comprising surfactants and/or suspending agents are utilized, such as in an amount sufficient to stabilize $SeS_2$ suspension in liquid and semi-solid dosage forms, such as in order to enable its topical application. However, use of surfactants results, in many instances, in negative consequences or adverse effects in ocular administration with selenium disulfide. In some preferred embodiments herein, compositions provided herein and/or administered in methods provided herein do not comprise surfactant. In certain instances, despite the lack of surfactant, compositions provided herein still provide therapeutically beneficial results, such as when administered in concentrations and/or volumes as described herein.

Methods for Treating Demodex or Disorders Thereof

In an aspect, provided herein is a method for treating Demodex or disorder in or around the eye in an individual in need thereof, the method comprising administering a therapeutically effective amount of a pharmaceutical composition to an ocular surface, surrounding ocular tissues, or a combination thereof of the individual; the pharmaceutical composition comprising a therapeutically effective amount of selenium disulfide ($SeS_2$) to reduce the population of Demodex or inhibit the overgrowth of Demodex; the pharmaceutical composition comprising the therapeutically effective amount of $SeS_2$ in a therapeutically effective concentration, the therapeutically effective concentration being about 0.1 wt. % to about 2010 wt. % (e.g., 0.1 wt. % to less than about 2.5 wt.)% to inhibit the overgrowth of Demodex or 2.5 wt. % to greater than about 5 wt. % to reduce the population of Demodex) of $SeS_2$; and the pharmaceutical composition being administered in a volume of about 25 microliters (μL) or less (e.g., preferably, less than 25 μL). In some embodiments, the pharmaceutical composition of $SeS_2$ at a therapeutically effective concentration to reduce the population of Demodex or inhibit the overgrowth of Demodex is administered in a volume of about 0.3 μL, about 5 μL, about 1.0 μL, about 1.5 μL, about 2.0 μL, about 2.5 μL, about 3.0 μL, about 3.5 μL, about 4.0 μL, about 4.5 μL, about 5.0 μL, about 5.5 μL, about 6.0 μL, about 6.5 μL, about 7.0 μL, about 7.5 μL, about 8.0 μL, about 8.5 μL, about 9.0 μL, about 9.5 μL, about 10.0 μL, about 10.5 μL, about 11.0 μL, about 11.5 μL, about 12.0 μL, about 12.5 μL, about 13.0 μL, about 13.5 μL, about 14.0 μL, about 14.5 μL, about 15.0 μL, about 15.5 μL, about 16.0 μL, about 16.5 μL, about 17.0 μL, about 17.5 μL, about 18.0 μL, about 18.5 μL, about 19.0 μL, about 19.5 μL, about 20.0 μL, about 20.5 μL, about 21.0 μL, about 21.5 μL, about 22.0 μL, about 22.5 μL, about 23.0 μL, about 23.5 μL, about 24.0 μL, about 24.5 μL, or about 25.0 μL.

In some embodiments, provided herein is a method for treating Demodex or disorder associated therewith in or around the eye of an individual in need thereof, the method comprising administering a therapeutically effective amount of a pharmaceutical composition to an ocular surface, surrounding ocular tissues (e.g., eyelid margin), or a combination thereof of the individual; the pharmaceutical composition comprising a therapeutically effective amount of selenium disulfide ($SeS_2$). In some embodiments, such method administration results in the reduction of the population or amount of Demodex. In some embodiments, the therapeutically effective concentration (e.g., to reduce the population of Demodex (e.g., by killing Demodex)) is about 2.5 wt. % to greater than about 5 wt. % of $SeS_2$; and the pharmaceutical composition being administered in a volume of about 25 microliters (μL) or less (e.g., preferably, less than 25 μL, such as about 0.3 μL to about 20 μL). In some embodiments, therapeutically effective of $SeS_2$ to reduce the population of is about 2.5 wt. %, about 3. wt. %, about 3.5 wt. %, about 4.0 wt. %, about 4.5 wt. %, about 5.0 wt. %, about 5.5 wt. %, about 6.0 wt. %, about 6.5 wt. %, about 7.0 wt. %, about 7.5 wt. %, about 8.0 wt. %, about 8.5 wt. %, about 9.0 wt. %, about 9.5 wt. %, about 10.0 wt. %, about 11.0 wt. %, about 11.5 wt. %, about 12.0 wt. %, about 12.5 wt. %, about 13.0 wt. %, about 13.5 wt. %, about 14.0 wt. %, about 14.5 wt. %, about 15.0 wt. %, about 15.5 wt. %, about 16.0 wt. %, about 16.5 wt. %, about 17.0 wt. %, about 17.5 wt. %, about 18.0 wt. %, about 18.5 wt. %, about 19.0 wt. %, about 19.5 wt. %, or about 20.0 wt. %. In some embodiments, the pharmaceutical composition of $SeS_2$ at a therapeutically effective concentration to reduce the population of Demodex is administered in a volume of about 0.3 μL, about 5 μL, about 0.0 μL, about 1.5 μL, about 2.0 μL, about 2.5 μL, about 3.0 μL, about 3.5 μL, about 4.0 μL, about 4.5 μL, about 5.0 μL, about 5.5 μL, about 6.0 μL, about 6.5 μL, about 7.0 μL, about 7.5 μL, about 8.0 μL, about 8.5 μL, about 9.0 μL, about 9.5 μL, about 10.0 μL, about 10.5 μL, about 11.0 μL, about 11.5 μL, about 12.0 μL, about 12.5 μL, about 13.0 μL, about 13.5 μL, about 14.0 μL, about 14.5 μL, about 15.0 μL, about 15.5 μL, about 16.0 μL, about 16.5 μL, about 17.0 μL, about 17.5 μL, about 18.0 μL, about 18.5 μL, about 19.0 μL, about 19.5 μL, about 0.0 μL, about 20.5 μL, about 21.0 μL, about 21.5 μL, about 22.0 μL, about 22.5 μL, about 23.0 μL, about 23.5 μL, about 24.0 μL, about 24.5 μL, or about 25.0 μL. In some instances, such a process (e.g., involving the use of reducing (or killing) concentrations of selenium disulfide) is performed by a clinician.

In certain embodiments, provided herein is a method for treating Demodex or disorder associated therewith in or around the eye of an individual in need thereof, the method comprising administering a therapeutically effective amount of a pharmaceutical composition to an ocular surface, surrounding ocular tissues, or a combination thereof of the individual; the pharmaceutical composition comprising a therapeutically effective amount of selenium disulfide ($SeS_2$); the pharmaceutical composition comprising the therapeutically effective amount of $SeS_2$ in a therapeutically effective concentration. In specific embodiments, the therapeutically effective concentration is effective to reduce the population or amount (or inhibit overgrowth thereof) of Demodex (e.g., by repelling or otherwise deterring some or all Demodex from infiltrating the treated location). A therapeutically effective concentration of $SeS_2$ can inhibit overgrowth of Demodex. In specific embodiments, the therapeutically effective concentration (e.g., to inhibit the overgrowth of Demodex) is about 0.01 wt. % to about 2.5 wt. % of $SeS_2$. In some embodiments, the therapeutically effective concentration of $SeS_2$ to inhibit the overgrowth of Demodex is about 0.01 wt. %, about 0.02 wt. %, about 0.03 wt. %, about 0.04 wt. %, about 0.05 wt. %, about 0.06 wt. %, about 0.07 wt. %, about 0.08 wt. %, about 0.09 wt. %, about 0.1 wt. %, about 0.2 wt. %, about 0.3 wt. %, about 0.4 wt. %, about 0.5 wt. %, about 0.6 wt. %, about 0.7 wt. %, about 0.8 wt. %, about 0.9 wt. %, about 1.0 wt. %, about 1.1 wt. %, about 1.2 wt. %, about 1.3 wt. %, about 1.4 wt. %, about 1.5 wt. %, about 1.6 wt. %, about 1.7 wt. %, about 1.8 wt. %, about 1.9 wt. %, about 2.0 wt. %, about 2.1 wt. %, about 2.2 wt. %, about 2.3 wt. %, about 2.4 wt. %, or about 2.5 wt. % In some embodiments, the pharmaceutical composition is administered in a volume of about 25 microliters (μL) or less (e.g., preferably, less than 25 μL, such as about 0.3 μL to about 20 μL. In some embodiments, the pharmaceutical composition of $SeS_2$ at a therapeutically effective concentration to inhibit the overgrowth of Demodex is administered in a volume of about 0.3 μL, about 5 μL, about 1.0 μL, about 1.5 μL, about 2.0 μL, about 2.5 μL, about 3.0 μL, about 3.5 μL, about 4.0 μL, about 4.5 μL, about 5.0 μL, about 5.5 μL, about 6.0 μL, about 6.5 μL, about 7.0 μL, about 7.5 μL, about 8.0 μL, about 8.5 μL, about 9.0 μL, about 9.5 μL, about 10.0 μL, about 10.5 μL, about 11.0 μL, about 11.5 μL, about 12.0 μL, about 12.5 μL, about 13.0 μL, about 13.5 μL, about 14.0 μL, about 14.5 μL, about 15.0 μL, about 15.5 μL, about 16.0 μL, about 16.5 μL, about 17.0 μL, about 17.5 μL, about 18.0 μL, about 18.5 μL, about 19.0 μL, about 19.5 μL, about 20.0 μL, about 20.5 μL, about 21.0 μL, about 21.5 μL, about 22.0 μL, about 22.5 μL, about 23.0 μL, about 23.5 μL, about 24.0 μL, about 24.5 μL, or about 25.0 μL. In some instances, such a process (e.g., involving the use of lower concentrations of selenium disulfide) is performed by a non-clinician, such as the person to whom the composition is applied (e.g., home use).

In some embodiments, a method provided herein comprises administration of a pharmaceutical composition and a second pharmaceutical composition (e.g., subsequent to the administration of the first concentration, such as at least one day later). In certain embodiments, the first composition is a high concentration (e.g., about 2.5 wt. % to about 5 wt. % selenium disulfide) and the second composition is a low (or inhibiting (or repelling)) concentration (e.g., about 0.1 wt. % to about 2.5 wt. % selenium disulfide).

In another aspect, provided herein is a method for treating Demodex or disorder associated therewith in or around the eye of an individual in need thereof, the method comprising administering in a dosing regimen a therapeutically effective amount of a pharmaceutical composition to an ocular surface, surrounding ocular tissues, or a combination thereof of the individual; the pharmaceutical composition comprising a therapeutically effective amount of selenium disulfide ($SeS_2$); the pharmaceutical composition comprising the therapeutically effective amount of $SeS_2$ in a therapeutically effective concentration, the therapeutically effective concentration being about 0.1 wt. % to about 2.5 wt. %; and during each administration of the dosing regimen, the pharmaceutical composition being administered in a volume of about 25 microliters (μL) or less (e.g., preferably, less than 25 μL).

In some embodiments, the individual is more prone to develop Demodex depending on biotic or abiotic environmental factors (e.g., temperature, sun-damage, microenvironment (e.g., bacteria, parasites, mites), diet, etc.). In some embodiments, the disorder associated with Demodex in or around the eye is, for example, Blepharitis, Seborrheic Blepharitis, or the like, or any combination thereof. In some embodiments, the disease or disorder in or around the eye is associated with hyperkeratosis, keratoconjunctivitis, blepharitis, or any combination thereof.

In some embodiments, the therapeutically effective concentration comprises at least about 0.01 wt. %, about 0.05 wt. %, about 0.1 wt. %, about 0.15 wt. %, about 0.2 wt. %, about 0.25 wt. %, about 0.3 wt. %, about 0.35 wt. %, about 0.4 wt. %, about 0.45 wt. %, about 0.5 wt. %, about 0.55 wt. %, about 0.6 wt. %, about 0.65 wt. %, about 0.7 wt. %, about 0.75 wt. %, about 0.8 wt. %, about 0.85 wt. %, about 0.9 wt. %, about 0.95 wt. %, about 1.0 wt. %, about 1.25 wt. %, about 1.5 wt. %, about 1.75 wt. %, about 2.0 wt. %, about 2.5 wt. %, about 3.0 wt. %, about 4.0 wt. %, or more of selenium disulfide ($SeS_2$). In some embodiments, the therapeutically effective concentration comprises at most about 5.0 wt. %, about 4.0 wt. %, about 3.0 wt. %, about 2.5 wt. %, about 2.0 wt. %, about 1.75 wt. %, about 1.5 wt. %, about 1.25 wt. %, about 1.0 wt. %, about 0.95 wt. %, about 0.9 wt. %, about 0.85 wt. %, about 0.8 wt. %, about 0.75 wt. %, about 0.70 wt. %, about 0.65 wt. %, about 0.60 wt. %, about 0.55 wt. %, about 0.5 wt. %, about 0.45 wt. %, about 0.4 wt. %, about 0.35 wt. %, about 0.3 wt. %, about 0.25 wt. %, or less. In some embodiments, the therapeutically effective concentration comprises from about 0.01 wt. % to about 10.0 wt. %, about 0.01 wt. % to about 5.0 wt. %, about 0.01 wt. % to about 2.5 wt. %, about 0.5 wt. % to about 2.5 wt. %, about 0.5 wt. % to about 1.0 wt. %.

In some embodiments, the therapeutically effective concentration to reduce Demodex (e.g., to terminate Demodex) is at least about 2.5 wt. %, at least about 3 wt. %, at least about 3.5 wt. %, at least about 4 wt. %, at least about 4.5 wt. %, or at least about 5 wt. % or more of selenium disulfide ($SeS_2$), such as up to about 7.5 wt. %, up to about 7 wt. %, up to about 6 wt. %, or up to about 5 wt. %. In some embodiments, the therapeutically effective concentration to inhibit the overgrowth of Demodex (e.g., to repel Demodex) comprises at least about 0.05 wt. %, at least about 0.1 wt. %, at least about 0.2 wt. %, at least about 0.3 wt. %, at least about 0.4 wt. %, at least about 0.5 wt. %, at least about 0.6 wt. %, at least about 0.7 wt. %, at least about 0.8 wt. %, at least about 0.9 wt. %, at least about 1 wt. or more of selenium disulfide ($SeS_2$), such as up to about 3 wt. %, up to about 2.5 wt. %, or up to about 2 wt. %.

In some embodiments, the volume of the pharmaceutical composition or the volume of pharmaceutical composition administered using a method provided herein is at most about 30 μL, 25 μL (e.g., less than 25 μL), at most about 20 μL, at most about 15 μL, at most about 10 μL, at most about 5 μL, at most about 4 μL, at most about 3 μL, at most about 2 μL, at most about 1 μL, at most about 0.5 μL, or the like. In some embodiments, the volume is at least about 0.01 microliters (μL), at least about 0.05 μL, at least about 0.1 μL, at least about 0.2 μL, at least about 0.3 μL, at least about 0.4 μL, at least about 0.5 μL, at least about 1 μL, at least about 5 μL, about 10 μL, about 15 μL, about 20 μL, or more. In some embodiments, the volume is from about 0.01 μL to about 50 μL, about 0.1 μL to about 30 μL, about 0.5 μL to 25 μL (e.g., less than 25 μL), about 1 μL to 25 μL (e.g., less than 25 μL), about 10 μL to 25 μL (e.g., less than 25 μL), about 0.5 μL to about 1 IL, about 0.5 μL to about 2 μL, about 0.5 μL to about 5 μL, about 2 μL to about 5 μL, about 4 μL to about 12 μL, about 10 μL to about 15 μL, about 15 μL to about 20 μL, about 20 μL to about 25 μL, about 1 μL to less than 25 μL, about 10 μL to less than 25 μL, or about 2.5 μL to about 10 μL, or about 2.5 μL to about 10 μL. In some embodiments the pharmaceutical composition is a discrete pharmaceutical composition.

In some embodiments, the therapeutically effective amount of $SeS_2$ is at least about 1 microgram (μg), at least about 1.5 micrograms (μg), at least about 2 micrograms (μg), at least about 2.5 micrograms (μg), at least about 3 micrograms (μg), at least about 3.5 micrograms (μg), at least about 4 micrograms (μg), at least about 5 micrograms (μg), at least about 10 micrograms (μg), at least about 20 micrograms (μg), at least about 30 micrograms (μg), at least about 40 micrograms (μg), at least about 50 micrograms (μg), at least about 60 micrograms (μg), at least about 70 micrograms (μg), at least about 80 micrograms (μg), at least about 90 micrograms (μg), at least about, at least about 0.1 milligrams (mg), at least about 0.2 mg, at least about 0.3 mg, at least about 0.44 mg, at least about 0.5 mg, at least about 0.6 mg, at least about 0.7 mg, at least about 0.8 mg, at least about 0.9 mg, at least about 1 mg, at least about 2 mg, at least about 2.5 mg, or the like. In some embodiments, the therapeutically effective amount of selenium disulfide ($SeS_2$) is about 25 mg or less, about 15 mg or less, about 10 mg or less, 7.5 mg or less, about 5 mg or less, about 1 mg or less, about 0.1 mg or less, about 50 micrograms or less, about 25 micrograms or less, about 15 micrograms or less, about 10 micrograms or less, about 5 micrograms or less, about 2 micrograms or less, about 1.5 micrograms or less, or about 1 microgram or less. In some embodiments, the therapeutically effective amount of $SeS_2$ is 1 microgram, about 2 micrograms, about 5 micrograms, about 10 micrograms, about 20 micrograms, about 40 micrograms, about 80 micrograms, about 0.1 mg, about 0.2 mg, about 0.3 mg, about 0.4 mg, about 0.5 mg, about 1 mg, about 2 mg, about 3 mg, about 4 mg, about 5 mg, about 6 mg, about 8 mg, about 10 mg, or the like. In some embodiments, the therapeutically effective amount of $SeS_2$ is about 4 mg.

In some embodiments, the pharmaceutical composition is an ointment. In some embodiments, the ointment is, for example, hydrocarbon based, absorption based, water-soluble based, emulsifying based, or vegetable based. In some embodiments, the ointment comprises, for example, a hard paraffin, a soft paraffin, a microcrystalline wax, a cersine, a wool fat, a beeswax, a macrogol, an emulsifying wax, olive oil, coconut oil, sesame oil, almond oil, peanut oil, or any combination thereof. In some embodiments, the ointment is a soft paraffin, such as, for example, petroleum jelly or petrolatum.

In some embodiments, the pharmaceutical composition is provided using a device that delivers a volume of at most about 30 μL, 25 μL (e.g., less than 25 μL), at most about 20 μL, at most about 15 μL, at most about 10 μL, at most about 5 μL, at most about 2 μL, at most about 1 μL, at most about 0.5 μL, at most about 0.4 μL, at most about 0.3 μL, at most about 0.2 μL, at most about 0.1 μL, at most about 0.05 μL, at most about 0.01 μL or the like. In some embodiments, the pharmaceutical composition is provided using a device that delivers a volume of at least about 0.01 microliters (μL), at least about 0.05 μL, at least about 0.1 μL, at least about 0.5 μL, at least about 1 μL, at least about 5 μL, about 10 μL, about 15 μL, about 20 μL, or more. In some embodiments, the pharmaceutical composition is provided using a device that delivers a volume from about 0.01 μL to about 50 μL, about 0.1 μL to about 30 μL, about 0.5 μL to 25 μL (e.g., less than 25 μL), about 1 μL to 25 μL (e.g., less than 25 μL), about 10 μL to 25 μL (e.g., less than 25 μL), about 0.5 μL to about 1 μL, about 0.5 μL to about 2 μL, about 0.5 μL to about 5 μL, about 2 μL to about 5 μL, about 4 μL to about 12 μL, about 10 μL to about 15 μL, about 15 μL to about 20 μL, about 20 μL to about 25 μL, about 1 μL to less than 25 μL, about 10 μL to less than 25 μL, or about 2.5 μL to about 10 μL or about 2.5 μL to about 10 μL. In some embodiments the pharmaceutical composition is provided using a device that delivers a discrete volume. In some embodiments, the pharmaceutical composition is provided using a device that delivers a volume of about 25 μL or less (e.g., preferably, less than 25 μL). In some embodiments, the device delivers a volume of about 5 μL. In some embodiments, the device delivers a volume of about 0.5 μL. In some embodiments, the device delivers a volume of about 0.4 μL. In some embodiments, the device delivers a volume of about 0.3 μL.

In some embodiments, the pharmaceutical composition is administered to an eyelid of the individual, an eyelash of the individual, or a combination thereof. In some embodiments, the pharmaceutical composition is administered to an eyelid of the individual. In some embodiments, the pharmaceutical composition is administered to more than one eyelid of the individual. In some embodiments, the pharmaceutical composition is administered to each eyelid of the individual. In some embodiments, the pharmaceutical composition is administered to an eyelash of the individual. In some embodiments, the pharmaceutical composition is administered to more than one eyelash of the individual. In some embodiments, the pharmaceutical composition is administered to each eyelash of the individual. In some embodiments, the pharmaceutical composition is administered to both an eyelid and an eyelash of the individual. In some embodiments, the pharmaceutical composition is administered to each eyelid and to each eyelash of the individual. In some embodiments, the pharmaceutical composition is delivered to an eyelid margin of the eyelid. In some embodiments, the pharmaceutical composition is delivered to an eyelid margin of each eyelid. In some embodiments, the pharmaceutical composition is delivered to an eyelid margin of the eyelid and an eyelash of the individual. In some embodiments, the pharmaceutical composition is delivered to an eyelid margin of each eyelid and each eyelash of the individual.

In some embodiments, the pharmaceutical composition is administered by the individual receiving treatment of the pharmaceutical composition. In some embodiments, the individual applies the pharmaceutical composition using an applicator. In some embodiments, the applicator is an object that aids in delivering the pharmaceutical composition to an eyelid of the individual, an eyelash of the individual, or a combination thereof. In some embodiments, the individual applies the pharmaceutical composition using a finger.

In some embodiments, the pharmaceutical composition does not comprise a surfactant. In some embodiments, the pharmaceutical composition comprises a surfactant that does not cause irritation to the eye or the surrounding tissue.

In some embodiments, the pharmaceutical composition does not cause substantial keratitis and/or keratoconjunctivitis. Substantial keratitis and/or keratoconjunctivitis as described herein can refer to symptoms of keratitis and/or keratoconjunctivitis experienced by an individual or symptoms experienced by at least 30%, at least 40%, at least 50%, at least 60%, at least 70%, at least 80%, at least 90%, or at least 99% of individuals impacted by a disorder involving Demodex.

In some embodiments, the pharmaceutical composition does not cause symptoms of keratitis and/or keratoconjunctivitis such as substantial redness to the eye. In some embodiments, the pharmaceutical composition does not cause symptoms of keratitis and/or keratoconjunctivitis such as substantial irritation to the eye, the surrounding tissue, or a combination thereof. In some embodiments, the pharmaceutical composition reduce (e.g., relative to otherwise similar administration methods utilizing larger, such as at least 50% larger, at least 100% larger, at least 150% larger, at least 200% larger, or the like, volumes of pharmaceutical compositions) or eliminate side-effects that result in discontinued usage and/or compliance with a therapeutic protocol, such as described herein.

In some embodiments, the dosing regimen comprises administration of the pharmaceutical composition at least a first time and at least a second time. In some embodiments, at least the second time is subsequent to at least the first time, such as by at least about 15 minutes, about 30 minutes, about 1 hour, about 2 hours, about 4 hours, about 6 hours, about 12 hours, about 24 hours, 36 hours, 48 hours, 72 hours, 5 days, 7 days, or more. In some embodiments, at least the second time is subsequent to at least the first time, such as by at most about 7 days, about 5 days, about 72 hours, about 48 hours, about 36 hours, about 24 hours, about 12 hours, about 6 hours, 4 hours, 2 hours, 1 hour, 30 minutes, 15 minutes, or less. In some embodiments, at least the second time is subsequent to at least the first time, such as from about 7 days to 15 minutes, about 2 days to 30 minutes, about 24 hours to about 1 hour, or about 24 hours to about 12 hours. In some embodiments, the pharmaceutical composition administered the first time is applied at a different time point than the pharmaceutical composition administered the second time (e.g., and additional, such as third, fourth, fifth, etc., times). For example, the administration of the pharmaceutical composition a first and a second time may not indicate that a particular dose is administered twice during the same administration of the particular dose, but rather that a full dose (e.g., having the volume parameters provided herein) is administered a first time and another full dose (e.g., having the volume parameters provided herein) is administered a second time, each of which doses may be applied at an indicated dosing interval.

In some embodiments, the dosing regimen comprises administration of the pharmaceutical composition until the Demodex infestation is decreased. In some embodiments, the dosing regimen comprises administration of the pharmaceutical composition until the meibomian gland secretion is improved. In some embodiments, the dosing regimen comprises administration of the pharmaceutical composition prevents recurrence of the Demodex infestation. In some embodiments, the dosing regimen comprises administration of the pharmaceutical composition until the Demodex or disorder thereof is cured.

In some embodiments, the dosing regimen comprises administration of the pharmaceutical composition at least once-weekly for at least two administrations, at least 3 administration, at least 4 administration, at least 5 administrations, at least 6 administrations, at least 7 administrations, at least 8 administrations, at least 9 administrations, at least 10 administrations, at least 20 administrations, at least 30 administrations, at least 40 administrations, at least 50 administrations, or more. In some embodiments, the dosing regimen is at least twice-weekly (e.g., three times weekly, four times weekly, five times weekly, etc.). In some embodiments, the dosing regimen is twice-weekly. In some embodiments, the dosing regimen is at least once-daily (e.g., twice daily, three times daily, four times daily, five times daily, etc.). In some embodiments, the dosing regimen is several times a day.

Pharmaceutical Compositions

In certain aspects, provided herein is a pharmaceutical composition comprising a therapeutically effective amount of selenium disulfide ($SeS_2$), the pharmaceutical composition comprising the therapeutically effective amount of $SeS_2$ in a therapeutically effective concentration, the therapeutically effective concentration being about 0.1 wt. % to about 2.5 wt. % $SeS_2$, wherein the pharmaceutical composition comprises a volume (e.g., dose) of about 25 microliters (μL) or less (e.g., preferably, less than 25 μL).

In some embodiments, the pharmaceutical composition does not comprise a surfactant. In some embodiments, the pharmaceutical composition comprises a surfactant that does not cause irritation to the eye or the surrounding tissue.

In some embodiments, the therapeutically effective concentration comprises at least about 0.01 wt. %, about 0.05 wt. %, about 0.1 wt. %, about 0.15 wt. %, about 0.2 wt. %, about 0.25 wt. %, about 0.3 wt. %, about 0.35 wt. %, about 0.4 wt. %, about 0.45 wt. %, about 0.5 wt. %, about 0.55 wt. %, about 0.6 wt. %, about 0.65 wt. %, about 0.7 wt. %, about 0.75 wt. %, about 0.8 wt. %, about 0.85 wt. %, about 0.9 wt. %, about 0.95 wt. %, about 1.0 wt. %, about 1.25 wt. %, about 1.5 wt. %, about 1.75 wt. %, about 2.0 wt. %, about 2.5 wt. %, about 3.0 wt. %, about 4.0 wt. %, or more of selenium disulfide ($SeS_2$). In some embodiments, the therapeutically effective concentration comprises at most about 5.0 wt. %, about 4.0 wt. %, about 3.0 wt. %, about 2.5 wt. %, about 2.0 wt. %, about 1.75 wt. %, about 1.5 wt. %, about 1.25 wt. %, about 1.0 wt. %, about 0.95 wt. %, about 0.9 wt. %, about 0.85 wt. %, about 0.8 wt. %, about 0.75 wt. %, about 0.70 wt. %, about 0.65 wt. %, about 0.60 wt. %, about 0.55 wt. %, about 0.5 wt. %, about 0.45 wt. %, about 0.4 wt. %, about 0.35 wt. %, about 0.3 wt. %, about 0.25 wt. %, or less. In some embodiments, the therapeutically effective concentration comprises from about 0.01 wt. % to about 10.0 wt. %, about 0.01 wt. % to about 5.0 wt. %, about 0.01 wt. % to about 2.5 wt. %, about 0.5 wt. % to about 2.5 wt. %, about 0.5 wt. % to about 1.0 wt. %.

In some embodiments, the volume of the pharmaceutical composition or the volume of pharmaceutical composition administered using a method provided herein is at most about 30 μL, 25 μL (e.g., less than 25 μL), at most about 20 μL, at most about 15 μL, at most about 10 μL, at most about 5 μL, or the like. In some embodiments, the volume is at least about 0.01 microliters (μL), at least about 0.05 μL, at least about 0.1 μL, at least about 0.3 μL, at least about 0.4 μL, at least about 0.5 μL, at least about 1 μL, at least about 5 μL, about 10 μL, about 15 μL, about 20 μL, or more. In some embodiments, the volume is from about 0.01 μL to about 50 μL, about 0.1 μL to about 30 μL, about 0.1 μL to about 0.5 μL, about 0.5 μL to 25 μL (e.g., less than 25 μL), about 1 μL to 25 μL (e.g., less than 25 μL), about 10 μL to 25 μL (e.g., less than 25 μL), or about 2.5 μL to about 10 μL. In some embodiments the pharmaceutical composition is a discrete pharmaceutical composition.

InIn some embodiments, the therapeutically effective amount of $SeS_2$ is at least about 1 microgram (μg), at least about 1.5 micrograms (μg), at least about 2 micrograms (μg), at least about 2.5 micrograms (μg), at least about 3 micrograms (μg), at least about 3.5 micrograms (μg), at least about 4 micrograms (μg), at least about 5 micrograms (μg), at least about 10 micrograms (μg), at least about 20 micrograms (μg), at least about 30 micrograms (μg), at least about 40 micrograms (μg), at least about 50 micrograms (μg), at least about 60 micrograms (μg), at least about 70 micrograms (μg), at least about 80 micrograms (μg), at least about 90 micrograms (μg), at least about 0.1 milligrams (mg), at least about 0.2 mg, at least about 0.3 mg, at least about 0.5 mg, at least about 1 mg, at least about 2 mg, at least about 2.5 mg, or the like. In some embodiments, the therapeutically effective amount of selenium disulfide ($SeS_2$) is about 25 mg or less, about 15 mg or less, about 10 mg or less, 7.5 mg or less, about 5 mg or less, about 1 mg or less, about 0.1 mg or less, about 50 micrograms or less, about 25 micrograms or less, about 15 micrograms or less, about 10 micrograms or less, about 5 micrograms or less, about 2 micrograms or less, about 1.5 micrograms or less, or about 1 microgram or less. In some embodiments, the therapeutically effective amount of $SeS_2$ is about 1 microgram, about 2 micrograms, about 5 micrograms, about 10 micrograms, about 20 micrograms, about 40 micrograms, about 80 micrograms, about 0.1 mg, about 0.2 mg, about 0.3 mg, about 0.4 mg, about 0.5 mg, about 1 mg, about 2 mg, about 3 mg, about 4 mg, about 5 mg, about 6 mg, about 8 mg, about 10 mg, or the like. In some embodiments, the therapeutically effective amount of $SeS_2$ is about 4 mg.

In some embodiments, the pharmaceutical composition is an ointment. In some embodiments, the ointment is, for example, hydrocarbon based, absorption based, water-soluble based, emulsifying based, or vegetable based. In some embodiments, the ointment comprises, for example, a hard paraffin, a soft paraffin, a microcrystalline wax, a cersine, a wool fat, a beeswax, a macrogol, an emulsifying wax, olive oil, coconut oil, sesame oil, almond oil, peanut oil, or any combination thereof. In some embodiments, the ointment is a soft paraffin, such as, for example, petroleum jelly or petrolatum.

In some embodiments, the pharmaceutical composition is provided using a device that delivers a volume of at most about 30 μL, 25 μL (e.g., less than 25 μL), at most about 20 μL, at most about 15 μL, at most about 10 μL, at most about 5 μL, at most about 2 μL, at most about 1 μL, at most about 0.5 μL, at most about 0.4 μL, at most about 0.3 μL, at most about 0.2 μL, at most about 0.1 μL, at most about 0.05 μL, at most about 0.01 μL or the like. In some embodiments, the pharmaceutical composition is provided using a device that delivers a volume of at least about 0.01 microliters (μL), at least about 0.05 μL, at least about 0.1 μL, at least about 0.5 μL, at least about 1 μL, at least about 5 μL, about 10 μL, about 15 μL, about 20 μL, or more. In some embodiments, the pharmaceutical composition is provided using a device that delivers a volume from about 0.01 μL to about 50 μL, about 0.1 μL to about 30 μL, about 0.5 μL to about less than 25 μL, about 0.5 μL to less than about 1 μL, about 0.5 μL to less than about 2 μL, about 0.5 μL to less than about 5 μL, about 2 μL to about 5 μL, about 4 μL to about 12 μL, about 10 μL to about 15 μL, about 15 μL to about 20 μL, about 20 μL to about 25 μL, about 1 μL to less than 25 μL, about 10 μL to less than 25 μL, or about 2.5 μL to about 10 μL. In some embodiments the pharmaceutical composition is provided using a device that delivers a discrete volume. In some embodiments, the pharmaceutical composition is provided using a device that delivers a volume of about 25 μL or less (e.g., preferably, less than 25 μL). In some embodiments, the device delivers a volume of about 5 μL. In some embodiments, the device delivers a volume of about 0.5 μL. In some embodiments, the device delivers a volume of about 0.4 μL. In some embodiments, the device delivers a volume of about 0.3 μL.

In some embodiments, the pharmaceutical composition does not cause substantial keratitis and/or keratoconjunctivitis. In some embodiments, the pharmaceutical composition does not cause substantial redness to the eye. In some embodiments, the pharmaceutical composition does not cause substantial irritation to the eye, the surrounding tissue, or a combination thereof. In some embodiments, the pharmaceutical composition is ophthalmically safe.

In certain embodiments, selenium disulfide has a composition that approximates to $SeS_2$. In some embodiments, the selenium disulfide comprises Se—S rings containing a variable number of S and Se atoms. In some embodiments, the number of Se to S atoms is 1 to 2, 1 to 3, 2 to 3, 2 to 4, 2 to 5, 3 to 5, 3 to 6, 3 to 7, 4 to 6, 4 to 7, 4 to 8, 4 to 9, 4 to 10, or, generally, $Se_nS_{8-n}$. In some embodiments, the selenium disulfide has a composition of 1, 2, 3-$Se_3S_5$. In some embodiments, 1, 2, 3-$Se_3S_5$ is contained in a ring structure. In some embodiments, the selenium disulfide has a composition of $SeS_2$.

In some embodiments, a pharmaceutical composition described herein further comprises a pharmaceutically suitable or acceptable carrier (e.g., a pharmaceutically suitable (or acceptable) excipient, physiologically suitable (or acceptable) excipient, or physiologically suitable (or acceptable) carrier). In some embodiments, any suitable excipient is optionally utilized, such as certain excipients described, for example, in Remington: The Science and Practice of Pharmacy (Gennaro, 21st Ed. Mack Pub. Co., Easton, Pa. (2005)).

Methods of Treatment Utilizing Stable Anhydrous Selenium Disulfide Compositions

Described herein are methods for treating Demodex or a disorder thereof in a patient in need comprising topical administration of a stable anhydrous selenium disulfide composition to the eyelid margin of the patient in need. In some embodiments, the composition is applied with the assistance of a health-care provider. An acute use, in one embodiment, requires a stronger stable anhydrous selenium disulfide formulation (either in terms of concentration of the selenium disulfide or the inherent activity of the selenium disulfide). A maintenance use, in one embodiment, allows for the use of lower concentrations of the selenium disulfide, or selenium disulfide with lower inherent activity. In one embodiment, the acute use is performed by the health care provider, and the maintenance use is performed by the patient or non-health care provider. In some embodiments, both the acute and maintenance use is performed by the patient or non-health care provider. In some embodiments, administration does not occur with the active assistance of a health care provider, but rather involves the patient applying the stable anhydrous selenium disulfide formulation to his/her eyelid margin. In one embodiment, such administration occurs over an extended period of time; one way of describing this patient-administered multi-administration mode is as a chronic use.

Provided herein is a method for treating Demodex or a disorder thereof in a patient in need thereof, comprising topically administering to the patient a composition that reaches the eyelid margin of the patient, wherein the composition comprises a therapeutically-effective amount of stable anhydrous selenium disulfide composition.

One embodiment provides the method wherein the concentration of the stable anhydrous selenium disulfide in the composition is between about 0.1 (wt.) % to about 10 (wt.) %, or other suitable concentration described herein.

One embodiment provides the method wherein composition is topically administered to the patient until the Demodex infestation is relieved. One embodiment provides the method wherein composition is topically administered to the patient periodically after relieving the Demodex infestation. One embodiment provides the method wherein the topical administration is a single administration. One embodiment provides the method wherein the topical administration is a periodic administration. One embodiment provides the method wherein the periodic administration is once a day. One embodiment provides the method wherein the periodic administration is two times a day.

Provided in certain embodiments herein, is a method for treating Demodex or a disorder thereof in a patient in need thereof, comprising topically administering to the patient a composition that reaches the eyelid margin of the patient, wherein the composition consists essentially of a therapeutically-effective amount of stable anhydrous selenium disulfide composition. One embodiment provides the method wherein the concentration of the stable anhydrous selenium disulfide in the composition is between about 0.10% to about 10%. One embodiment provides the method wherein composition is topically administered to the patient until the Demodex infestation is relieved. One embodiment provides the method wherein composition is topically administered to the patient periodically after relieving the Demodex infestation. One embodiment provides the method wherein the topical administration is a single administration. One embodiment provides the method wherein the topical administration is a periodic administration. One embodiment provides the method wherein the periodic administration is once a day. One embodiment provides the method wherein the periodic administration is two times a day.

Provided herein is a method for removing a Demodex infestation in a patient in need thereof, comprising topically administering to the patient a composition that reaches the eyelid margin of the patient, wherein the composition comprises a therapeutically-effective amount of stable anhydrous selenium disulfide composition. One embodiment provides the method wherein the concentration of the stable anhydrous selenium disulfide in the composition is between about 0.1% to about 10%. One embodiment provides the method wherein composition is topically administered to the patient until the Demodex infestation is relieved. One embodiment provides the method wherein composition is topically administered to the patient periodically after relieving the Demodex infestation. One embodiment provides the method wherein the topical administration is a single administration. One embodiment provides the method wherein the topical administration is a periodic administration. One embodiment provides the method wherein the periodic administration is once a day. One embodiment provides the method wherein the periodic administration is two times a day.

In some embodiments, topical administration of the composition comprising a selenium disulfide pharmacological agent and an anhydrous semi-solid ophthalmic base occurs twice a week. In some embodiments, topical administration of the composition comprising a selenium disulfide pharmacological agent and an anhydrous semi-solid ophthalmic base occurs every other day. In some embodiments, topical administration of the composition comprising a selenium disulfide pharmacological agent and an anhydrous semi-solid ophthalmic base occurs every day. In some embodiments, topical administration of the composition comprising a selenium disulfide pharmacological agent and an anhydrous semi-solid ophthalmic base occurs several times a day.

In some embodiments, the composition for topical administration is a liquid or a semi-solid. In some embodiments, the composition for topical administration is an emulsion semi-solid. In some embodiments, the composition for topical administration is a cream. In some embodiments, the composition for topical administration is an ointment. In some embodiments, meibomian gland opening pharmacological agent is suspended within the composition. In some embodiments, the composition for topical administration is a lotion. In some embodiments, the composition for topical administration is a gel. In some embodiments, the composition for topical administration is an anhydrous dispersion. In some embodiments, the composition for topical administration is an anhydrous lip balm or stick formulation or a device that enable the patient to target the eyelid margin.

One embodiment provides a method for treating a hyperkeratosis disorder associated with a Demodex infestation in a patient in need thereof comprising topically administering to the eyelid margin of the patient a composition comprising a therapeutically-effective amount of a stable anhydrous selenium disulfide formulation, wherein the hyperkeratosis disorder is selected from meibomian gland dysfunction, rosacea, blepharits, or acne. Another embodiment provides the method wherein the hyperkeratosis disorder is meibomian gland dysfunction.

In some embodiment, the method comprises treatment in an acute treatment scenario. In another embodiment, the method comprises treatment of a patient naïve to similar or identical treatment. In another embodiment, the method comprises treatment in a chronic treatment scenario. In another embodiment, the method comprises treatment in a maintenance therapy scenario. In an acute treatment scenario, the administered dosage of lipogenesis and lipid secretion enhancing selenium disulfide-containing (e.g., selenium disulfide ($SeS_2$)) drug or pharmaceutical agent may be higher than the administered dosage of lipogenesis and lipid secretion enhancing selenium disulfide-containing (e.g., selenium disulfide ($SeS_2$)) drug or pharmaceutical agent employed in a chronic treatment scenario or a maintenance therapy scenario. In an acute treatment scenario, the lipogenesis and lipid secretion enhancing selenium disulfide-containing (e.g., selenium disulfide ($SeS_2$)) drug or pharmaceutical agent may be different from the lipogenesis and lipid secretion selenium disulfide-containing (e.g., selenium disulfide ($SeS_2$)) drug or enhancing pharmaceutical agent employed in a chronic treatment scenario. In some embodiments, the course of therapy begins in the initial phase of therapy as an acute treatment scenario and later transitions into a chronic treatment scenario or a maintenance therapy scenario.

In certain clinical presentations, patients may require an initial treatment administered by a physician or healthcare professional, either by placing a more highly concentrated composition of one of the therapeutic agents described herein. In the event the higher concentration compositions are required, the application thereof may require ocular shielding or other activity to minimize the impact of irritation or disruption of the ocular surface or surrounding tissues. Following such a procedure, a patient may be given a different composition of active agent to take home to apply periodically to the lid margin to maintain the patency of the Demodex. Such application may occur twice daily, once a day, weekly or monthly, depending on the composition activity and the desired product profile of the therapy.

One aspect of the methods of treatment described herein is the location of the topical administration of the composition. In one embodiment, the composition comprising a lipogenesis and lipid secretion enhancing selenium disulfide-containing (e.g., selenium disulfide ($SeS_2$)) drug or pharmaceutical agent is administered such that no irritation to eye occurs. In one embodiment, the composition comprising a lipogenesis and lipid secretion enhancing selenium disulfide-containing (e.g., selenium disulfide ($SeS_2$)) drug or pharmaceutical agent is administered to the eyelid margin.

One additional embodiment of the methods of treatment described herein is the use of a protective element provided to the eye to avoid irritation to the eye. Although the compositions described herein are generally non-irritating, in some embodiments (e.g., high concentration of agent or when used on a sensitive eye) a protective element provides an additional layer of safety and comfort for the patient. In one embodiment, the composition comprising a lipogenesis and lipid secretion enhancing selenium disulfide-containing (e.g., selenium disulfide ($SeS_2$)) drug or pharmaceutical agent is administered while an eye shield is placed on the eye to reduce contact of the agent with the cornea and/or conjunctiva such that reduced irritation to eye occurs. In some embodiments, the eye shield is a contact lens or an eye covering. In some embodiments, the eye covering comprises a self-adhesive. In one embodiment, the composition comprising a lipogenesis and lipid secretion enhancing selenium disulfide-containing (e.g., selenium disulfide ($SeS_2$)) drug or pharmaceutical agent is administered while the lid is pulled away from the globe to reduce contact of the agent with the cornea and/or conjunctiva such that reduced irritation to eye occurs.

Accurate dosing of small amounts of semi-solid products has been difficult to achieve due to the high viscosity and non-Newtonian aspects of such semi-solids. Further, as such dosing mechanisms are currently large and expensive, their use for the treatment of temporary conditions, or for short-term clinical trials are limited. Excessive application of many semi-solid products may cause unwanted side-effects. For example, excessive application of eye products may blur vision by creating thick layers that mixes into the tear film. Insufficient application of many products may slow or prevent proper treatment. Additionally, controlled dispensed volumes may further improve the application accuracy for proper treatment. For example, excessive eye medicament applied to the eye may be accidentally applied to the eye-lid margin. Finally, many such medicaments are sensitive to dirt, particulate, and oils, and must be transferred directly to the treatment site without contact with non-applicator surfaces, to avoid contamination.

Many semi-solid products are stored and dispensed from product tubes, which are often improper for accurate dosing. As such product tubes may be formed of metal, plastic, or both, the internal dispensing pressure may continue or reverse once the force applied by the user terminates.

As such, provided herein are intuitive, cost-effective dispensing aids, systems, and method which enable accurately control the semi-solid product dosing.

Methods for Precise Secretion of a Semi-Solid Product

Provided herein in some embodiments is a method for precise secretion of a semi-solid product comprising: providing a product tube; inserting the dispensing tip of the product tube within the aperture of a dispenser; aligning a shoulder of the product tube against a proximal surface of the dispenser; and compressing the product tube to secrete the semi-solid product until the semi-solid product is level with a proximal portion of the first hyperacuity target, a proximal portion of the second hyperacuity target, or both.

In some embodiments, the method further comprises removing the secreted semi-solid product from the product tube. In some embodiments, removing the secreted semi-solid product from the product tube comprises removing the secreted semi-solid product from the product tube with an applicator or a finger. In some embodiments, the method further comprises applying the semi-solid product to a patient. In some embodiments, the product tube further comprises a cap, and wherein the method further comprises removing the cap. In some embodiments, the cap is removed before inserting the dispensing tip of the product tube within the aperture of the dispenser. In some embodiments, the cap is removed after inserting the dispensing tip of the product tube within the aperture of the dispenser. In some embodiments, the method further comprises replacing the cap onto the product tube after removing the secreted semi-solid product from the product tube. In some embodiments, the semi-solid product generally maintains its cylindrical shape once it is secreted from the nozzle of the product tube.

In some embodiments, the method further comprises removing the secreted semi-solid product from the product tube. In some embodiments, removing the secreted semi-solid product from the product tube comprises removing the secreted semi-solid product from the product tube with an applicator or a finger. In some embodiments, the method further comprises applying the semi-solid product to a patient. In some embodiments, the product tube further comprises a cap, and wherein the method further comprises removing the cap. In some embodiments, the method further comprises replacing the cap onto the product tube after removing the secreted semi-solid product from the product tube. In some embodiments, the semi-solid product generally maintains its cylindrical shape once it is secreted from the nozzle of the product tube.

Stable Anhydrous Selenium Disulfide Formulations

Described herein in some embodiments are stable anhydrous formulations of selenium disulfide which are chemically stable, substantially free of aggregates and agglomerates. In some embodiments, the stable anhydrous selenium sulfide formulations described herein are substantially free of surfactants. In some embodiments, the stable anhydrous selenium sulfide formulations described herein are substantially free of dispersing agents. In some embodiments, the stable anhydrous selenium disulfide formulations described herein, contain about 0.01 (wt. %) to about 5 (wt.) % selenium disulfide. In some embodiments, the stable anhydrous selenium disulfide formulations described herein, contain about 2.5 (wt.) % selenium disulfide. In some embodiments, the stable anhydrous selenium disulfide formulations described herein, contain about 0.01 (wt.) % to about 10 (wt.) % selenium disulfide. In some embodiments, the stable anhydrous selenium disulfide formulations described herein, contain about 0.01 (wt.) % selenium disulfide. In some embodiments, the stable anhydrous selenium disulfide formulations described herein, contain about 0.05 (wt.) % selenium disulfide. In some embodiments, the stable anhydrous selenium disulfide formulations described herein, contain about 0.1 (wt.) % selenium disulfide. In some embodiments, the stable anhydrous selenium disulfide formulations described herein, contain about 0.5 (wt.) % selenium disulfide. In some embodiments, the stable anhydrous selenium disulfide formulations described herein, contain about 1.0 (wt.) % selenium disulfide. In some embodiments, the stable anhydrous selenium disulfide formulations described herein, contain about 1.5 (wt.) % selenium disulfide. In some embodiments, the stable anhydrous selenium disulfide formulations described herein, contain about 2.0 (wt.) % selenium disulfide. In some embodiments, the stable anhydrous selenium disulfide formulations described herein, contain about 2.5 (wt.) % selenium disulfide. In some embodiments, the stable anhydrous selenium disulfide formulations described herein, contain about 3.0 (wt.) % selenium disulfide. In some embodiments, the stable anhydrous selenium disulfide formulations described herein, contain about 3.5 (wt.) % selenium disulfide. In some embodiments, the stable anhydrous selenium disulfide formulations described herein, contain about 4.0 (wt.) % selenium disulfide. In some embodiments, the stable anhydrous selenium disulfide formulations described herein, contain about 4.5 (wt.) % selenium disulfide. In some embodiments, the stable anhydrous selenium disulfide formulations described herein, contain about 5.0 (wt.) % selenium disulfide. In some embodiments, the stable anhydrous selenium disulfide formulations described herein, contain about 5.5 (wt.) % selenium disulfide. In some embodiments, the stable anhydrous selenium disulfide formulations described herein, contain about 6.0 (wt.) % selenium disulfide. In some embodiments, the stable anhydrous selenium disulfide formulations described herein, contain about 6.5 (wt.) % selenium disulfide. In some embodiments, the stable anhydrous selenium disulfide formulations described herein, contain about 7.0 (wt.) % selenium disulfide. In some embodiments, the stable anhydrous selenium disulfide formulations described herein, contain about 7.5 (wt.) % selenium disulfide. In some embodiments, the stable anhydrous selenium disulfide formulations described herein, contain about 8.0 (wt.) % selenium disulfide. In some embodiments, the stable anhydrous selenium disulfide formulations described herein, contain about 8.5 (wt.) % selenium disulfide. In some embodiments, the stable anhydrous selenium disulfide formulations described herein, contain about 9.0 (wt.) % selenium disulfide. In some embodiments, the stable anhydrous selenium disulfide formulations described herein, contain about 9.5 (wt.) % selenium disulfide. In some embodiments, the stable anhydrous selenium disulfide formulations described herein, contain about 10.0 (wt.) % selenium disulfide. In some embodiments, the stable anhydrous selenium disulfide formulations described herein, contain about 11.0 (wt.) % selenium disulfide. In some embodiments, the stable anhydrous selenium disulfide formulations described herein, contain about 12.0 (wt.) % selenium disulfide. In some embodiments, the stable anhydrous selenium disulfide formulations described herein, contain about 13.0 (wt.) % selenium disulfide. In some embodiments, the stable anhydrous selenium disulfide formulations described herein, contain about 14.0 (wt.) % selenium disulfide. In some embodiments, the stable anhydrous selenium disulfide formulations described herein, contain about 15.0 (wt.) % selenium disulfide. In some embodiments, the stable anhydrous selenium disulfide formulations described herein, contain about 16.0 (wt.) % selenium disulfide. In some embodiments, the stable anhydrous selenium disulfide formulations described herein, contain about 17.0 (wt.) % selenium disulfide. In some embodiments, the stable anhydrous selenium disulfide formulations described herein, contain about 18.0 (wt.) % selenium disulfide. In some embodiments, the stable anhydrous selenium disulfide formulations described herein, contain about 19.0 (wt.) % selenium disulfide. In some embodiments, the stable anhydrous selenium disulfide formulations described herein, contain about 20.0 (wt.) % selenium disulfide.

In some embodiments, the anhydrous semi-solid base is an oleaginous base. Oleaginous bases, for the stable anhydrous selenium disulfide formulations described herein may include petroleum base, mineral oil, a mixture of mineral oil and white petroleum, vegetable oil, petrolatum or petroleum jelly (Vaseline®). In some embodiments, the oleaginous base is petrolatum or petroleumielly. In some embodiments, the vegetable oil is chosen from coconut oil, fractionated coconut oil, jojoba oil, olive oil, sunflower oil, almond oil, cod liver oil, castor oil or virgin wax In some embodiments, the stable anhydrous selenium disulfide formulations further comprise an oil. In some embodiments, the oil is chosen from a triglycerides, diglyceride, monoglycerides, acetylated lanolin alcohol, alkyl benzoate, an alkyl octanoate, almond oil, an unsaturated or polyunsaturated oil, apricot stone oil, arachidyl behenate, arachidyl propionate, avocado oil, barley oil, basil oil, beeswax, benzyl laurate, benzyl myristate, benzyl palmitate, bis (octyldodecyl stearoyl) dimer dilinoleate, borage seed oil, butyl myristate, butyl stearate, C12-C15 alkyl benzoate, C12-C15 alkyl octanoate, calendula oil, camphor oil, canelle nut tree oil, canola oil, capric/caprylic triglycerides, caprylic/capric triglyceride castor oil, caprylyl methicone, cardamom oil, carrot oil, castor oil, cetearyl ethylhexanoate, cetearyl isononanoate, cetearyl octanoate, cetyl acetate, cetyl dimethicone, cetyl ethylhexanoate, cetyl lactate, cetyl myristate, cetyl octanoate, cetyl palmitate, cetyl ricinoleate, citronella oil, clary sage oil, clove oil, cocoglycerides, coconut oil, cod-liver oil, corn oil, cotton oil, cottonseed oil, cyclohexasiloxane, cyclomethicone, cyclomethicone 5-NF (cyclopentasiloxane), cyclotetrasiloxane, cypress oil, decyl oleate, diethyleneglycol, diethylhexanoate, diethyleneglycol diisononanoate, diethyleneglycol dioctanoate, diethylhexanoate, diethylhexyl adipate, diethylhexyl malate, diethylhexyl succinate, diisopropyl adipate, diisopropyl dimerate, diisopropyl sebacate, diisosteary dimer dilinoleate, diisostearyl fumerate, dimethicone, dimethyl polysiloxane, dioctyl malate, dioctyl sebacate, disopropyl adipate, dodecyl oleate, cyclotetrasiloxane (Dow Corning 244 Fluid), cyclohexasiloxane/cyclopentasiloxane (Dow corning 246 Fluid (d6+d5)), epoxy-modified silicone oil, ester derivatives of lanolic acid, ethylhexyl cocoate, ethylhexyl ethylhexanoate, ethylhexyl hydroxystarate, ethylhexyl isononanoate, ethylhexyl palmitate, ethylhexyl palmytate, ethylhexyl pelargonate, ethylhexyl stearate, evening primrose oil, fatty acid-modified silicone oil, flaxseed oil, fluoro group-modified silicone oil, frankincense oil, gelled mineral oil, ginger oil, glycereth triacetate, glycerol triheptanoate, glyceryl oleate, glyceryl trioctanoate, glyceryl triundecanoate, grape seed oil, grapefruit oil, groundnut oil, hazelnut oil, heavy mineral oil, hempseed oil, herring oil, hexadecyl stearate, hexyl laurate, hydrocarbon oils, hydrogenated castor oil, hyssop oil, isoamyl laurate, isocetearyl octanoate, isocetyl behenate, isocetyl lanolate, isocetyl palmitate, isocetyl salicylate, isocetyl stearate, isocetyl stearoyl stearate, isodecyl ethylhexanoate, isodecyl isononanoate, isodecyl oleate, isododecane, isohexadecane isododecane, isohexadecanol, isohexyl decanoate, isononyl isononanoate, isononyl octanoate, isoparaffm, isopropyl isostearate, isopropyl lanolate, isopropyl laurate, isopropyl myristate, isopropyl palmitate, isopropyl stearate, isosteary citrate, isosteary salicylate, isosteary tartarate, isostearyl behenate, isostearyl erucate, isostearyl glycolate, isostearyl isononanoate, isostearyl isostearate, isostearyl lactate, isostearyl linoleate, isostearyl linolenate, isostearyl malate, isostearyl neopentanoate, isostearyl palmitate, isotridecyl isononanoate, jasmine oil,lauryl lactate, lavender oil, lemon oil, light mineral oil, liquid paraffin, liquid triglycerides, lucerne oil, maize germ oil, maleated soybean oil, mandarin oil, manuka oil, marjoram oil, marrow oil, MCT oil, methylphenylpolysiloxane, millet oil, mineral oil, myristyl lactate, myristyl myristate, myristyl neopentanoate, myristyl propionate, myrrh oil, neopentylglycol dicaprate, neopentylglycol dicaprylate/dicaprate, neroli oil, nutmeg oil, octyl palmitate, octyl stearate, octyldodecanol, octyldodecyl behenate, octyldodecyl hydroxystearate, octyldodecyl myristate, octyldodecyl stearoyl stearate, oils from animal origin, oils of plant origin, oleyl erucate, oleyl lactate, oleyl oleate, olive oil, dimethiconol, palm oil, passionflower oil, peanut oil, rapeseed oil, rosehip oil, rye oil, safflower oil, sage oil, salmon oil, sesame oil, shea butter, silicone oils, soya oil, soybean oil, stearyl caprate, stearyl dimethicone, stearyl heptanoate, stearyl propionate, sunflower oil, sweet almond oil, synthetic isoalkane, sysymbrium oil, syzigium *aromaticum* oil, tangerine oil, tea tree oil, therapeutic oils, tocopheryl acetate, tocopheryl linoleate, tridecyl ethylhexanoate, tridecyl isononanoate, triisocetyl citrate, unsaturated or polyunsaturated oils, vanilla oil, *verbena* oil, walnut oil, wheat germ glycerides, wheat germ oil, white petrolatum and mixtures thereof.

In some embodiments, the stable anhydrous selenium disulfide formulations described herein, further comprise a silicone based excipient. In some embodiments, the silicone based excipient is chosen from dimethiconol, dimethicone, cyclopentasiloxane, decamethylcyclopentasiloxane, alkylmethyl siloxane copolyol, alkylmethyl siloxane and stearyltrimethylsilane or any silicone excipient blend suitable for the stable anhydrous selenium disulfide formulations according to the embodiments provided herein. In some embodiments, the silicone based excipient is dimethicone. In some embodiments, the silicone based excipient is stearyltrimethylsilane and stearyl alcohol.

In some embodiments, the stable anhydrous selenium disulfide formulations described herein further comprise a cellulose-derived solidifying agent. In some embodiments the cellulose-derived solidifying agent is microfibrillated cellulose. In some embodiments the cellulose-derived solidifying agent is nanocrystalline cellulose.

In some embodiments, the stable anhydrous selenium disulfide formulations described herein, further comprise a solidifying agent such as fumed silica, hydrogenated vegetable oils or waxes. In some embodiments, the fumed silica is Aerosil® fumed silica.

In some embodiments, the stable anhydrous selenium disulfide formulations described herein, further comprise squalene or squalene.

Preventing leakage of selenium disulfide from the eyelids to the ocular surface is not desirable since in some instances, its target, the Demodex mites, are only reached from the lid edge and, for example, spillage of the drug into the fomix' and onto the ocular surface reduces its effectiveness. Furthermore, in some instances, avoiding leakage of selenium disulfide onto the aqueous ocular surface is desired so it does not aggregate and create large particles that can cause discomfort. In some embodiments, the formulation has a specific melting point to allow stable and persistent presence of the ointment over the eyelid with minimal leak onto the ocular surface, yet, enables its penetration to the meibomian orifices, as well as liquefaction of the natural meibum lipids. Described herein in some embodiments is an ointment composition which is semi-solid at room temperature and has melting temperature between 33° C. to 36° C. In some embodiments is provided an ointment composition which is semi-solid at room temperature and has melting temperature between 33° C. to 46° C. In some embodiments is provided an ointment composition which is semi-solid at room temperature and has melting temperature between 33° C. to 38°

C. In some embodiments is provided an ointment composition which is semi-solid at room temperature and has melting temperature between 33° C. to 40° C. In some embodiments is provided an ointment composition which is semi-solid at room temperature and has melting temperature between 33° C. to 42° C. In some embodiments is provided an ointment composition which is semi-solid at room temperature and has melting temperature between 33° C. to 44° C. In some embodiments is provided an ointment composition which is semi-solid at room temperature and has melting temperature between 34° C. to 37° C. In some embodiments is provided an ointment composition which is semi-solid at room temperature and has melting temperature between 35° C. to 38° C. In some embodiments is provided an ointment composition which is semi-solid at room temperature and has melting temperature between 32° C. to 40° C. In some embodiments is provided an ointment composition which is semi-solid at room temperature and has melting temperature between 33° C. to 56° C., wherein the composition releases squalene or other liquid lipids upon contact with eyelid margin. In some embodiments the formulation has a melting point that is higher than the temperature of the ocular surface which is about 34° C. so it does not liquefy when it comes in contact with the ocular surface but below 37° C. so it can penetrate the meibomian gland orifices.

Thin Layer of Drug Over Lid Margin

Lipid ophthalmic drug formulations are typically not well tolerated by patients since they get mixed into the tear fluid and cause blurred vision and also stick to the eye lashes and cause unpleasant sensation. It is therefore desired to provide a formulation that will not cause either of these side effects. In one embodiment of the present invention the formulation has viscosity characteristics that cause it to spread over the lid margin at a thickness of between 25 and 200 microns and preferably around 100 microns to allow enough drug to be in contact with the orifices in the eyelid (e.g., the meibomian gland) while not creating a surplus of drug that would mix with the tear firm or stick to the eye lashes.

Agglomeration and Ophthalmic Compositions

Major problems related to ophthalmic compositions are crystallization and agglomeration of active ingredients during preparation as well as during storage. Crystallization or agglomeration of active pharmaceutical ingredient (API) leads to non-uniformity of dose, difficulty of administration, irritation to eye due to large drug particles and/or any ocular adverse effect due to high drug concentration or failure of treatment due to low drug concentration. Where the ophthalmic formulations are prepared as suspension, it is desirable to prepare the suspension in a manner such that the suspended particles do not agglomerate into larger ones upon storage. A particle size above 10 μm in diameter in an ophthalmic composition may result in a foreign body sensation in the eye following ocular application, causing reflex tearing. A reduction in particle size generally improves the patient comfort and acceptability of ophthalmic formulations. In addition, reduced particle size will increase the contact area between the selenium disulfide particles and the orifice of the meibomian gland thus increasing the effectiveness of the formulation.

In some instances, selenium disulfide forms agglomerates under aqueous conditions. In certain instances, contacting selenium disulfide with aqueous medium causes immediate and spontaneous aggregation, causing selenium disulfide particles, with an initial average diameter of 5 to 10 μm, to aggregate into large clumps of 50 to 500 μm average diameter.

In some embodiments, the stable anhydrous selenium disulfide formulations described herein are substantially free of agglomerates. In some embodiments, substantially free of agglomerates means that the average selenium disulfide particle diameter throughout the formulation is less than about 50 μm, less than about 45 μm, less than about 40 μm, less than about 35 μm, less than about 30 μm, less than about 25 μm, less than about 20 μm, less than about 15 μm, less than about 10 μm, less than about 9 μm, less than about 8 μm, less than about 7 μm, less than about 6 μm, or less than about 5 μm. In some embodiments, substantially free of agglomerates means that the average selenium disulfide particle diameter throughout the formulation is no more than about 50 μm, no more than about 45 μm, no more than about 40 μm, no more than about 35 μm, no more than about 30 μm, no more than about 25 μm, no more than about 20 μm, no more than about 15 μm, no more than about 10 μm, no more than about 9 μm, no more than about 8 μm, no more than about 7 μm, no more than about 6 μm, or no more than about 5 μm. In some embodiments, substantially free of agglomerates means that the average selenium disulfide particle diameter throughout the formulation is between about 5 μm and about 10 μm, or between about 5 μm and about 15 μm, or between about 10 μm and about 20 μm, or between about 5 μm and about 20 μm, or between about 15 μm and about 25 μm. In some embodiments, substantially free of agglomerates means that the formulation contains less than about 10%, less than about 9%, less than about 8%, less than about 7%, less than about 6%, less than about 5%, less than about 4%, less than about 3%, less than about 2.5%, less than about 2%, less than about 1.5%, less than about 1%, less than about 0.9%, less than about 0.8%, less than about 0.7%, less than about 0.6%, less than about 0.5%, less than about 0.5%, less than about 0.4%, less than about 0.3%, less than about 0.2%, or less than about 0.1% of agglomerates. In some embodiments, substantially free of agglomerates means that the selenium disulfide particle diameter increases no more than 10 times, no more than 9 times, no more than 8 times, no more than 7 times, no more than 6 times, no more than 5 times, no more than 4 times, no more than 3 times, no more than 2 times, or no more than 1.5 times upon formulation compared with the initial particle diameter.

In some embodiments, "substantially free of agglomerate" indicates that the formulation does not contains any selenium disulfide agglomerate. In some embodiments, the stable anhydrous selenium disulfide formulations described herein do not contain particles larger than 5 μm in diameter. In some embodiments, the stable anhydrous selenium disulfide formulations described herein do not contain particles larger than 10 μm in diameter. In some embodiments, the stable anhydrous selenium disulfide formulations described herein do not contain particles larger than 20 μm in diameter. In some embodiments, the stable anhydrous selenium disulfide formulations described herein do not contain particles larger than 10 μm in diameter and do not contain any surfactants and dispersing agents. In some embodiments, the stable anhydrous selenium disulfide formulations described herein is substantially free of surfactants and dispersing agents. In some embodiments, substantially free of surfactants and dispersing agents means that the formulation contains less than about 10 (wt.) % surfactants, dispersing agents, and combination thereof. In some embodiments, substantially free of surfactants and dispersing agents means that the formulation contains less than about 10 (wt.) %, less than about 9 (wt.) %, less than about 8 (wt.) %, less than about 7 (wt.) %, less than about 6 (wt.) %, less than about 5 (wt.) %, less than about 4 (wt.) %, less than about 3 (wt.) %, less than about 2.5 (wt.) %, less than about 2 (wt.) %, less than about 1.5 (wt.) %, less than about 1 (wt.) %, less than about 0.9 (wt.) %, less than about 0.8 (wt.) %, less than about 0.7 (wt.) %, less than about 0.6 (wt.) %, less than about 0.5 (wt.) %, less than about 0.4 (wt.) %, less than about 0.3 (wt.) %, less than about 0.2 (wt.) %, or less than about 0.1 (wt.) % surfactants, dispersing agents, and combination thereof. In specific embodiments, the composition comprises less than 1 (wt.) % surfactant. In more specific embodiments, the composition comprises less than 0.5 (wt.) % surfactant. In still more specific embodiments, the composition comprises less than 0.1 (wt.) % surfactant. In some embodiments, substantially free of surfactants and dispersing agents means that the formulation contains no more than about 10 (wt.) % surfactants, dispersing agents, and combination thereof. In some embodiments, substantially free of surfactants and dispersing agents means that the formulation contains no more than about 10 (wt.) %, no more than about 9 (wt.) %, no more than about 8 (wt.) %, no more than about 7 (wt.) %, no more than about 6 (wt.) %, no more than about 5 (wt.) %, no more than about 4 (wt.) %, no more than about 3 (wt.) 00 no more than about 2.5 (wt.) %, no more than about 2 (wt.) 00 no more than about 1.5 (wt.) 00 no more than about 1 (wt.) 00 no more than about 0.9 (wt.) 00 no more than about 0.8 (wt.) 00 no more than about 0.7 (wt.) 00 no more than about 0.6 (wt.) 00 no more than about 0.5 (wt.) 00 no more than about 0.4 (wt.) 00 no more than about 0.3 (wt.) 00 no more than about 0.2 (wt.) 0 or no more than about 0.1 (wt.) % surfactants, dispersing agents, and combination thereof. In some embodiments, "substantially free of surfactants and dispersing agents" indicates that the formulation does not contains any surfactants, dispersing agents, and combination thereof. In some embodiments, substantially free of surfactants and dispersing agents means that the formulation is free of surfactants, dispersing agents, and combination thereof.

In some embodiments, the stable anhydrous selenium disulfide formulations described herein comprise a dispersion of selenium disulfide in an anhydrous semi-solid base. In some embodiments, the selenium sulfide is dispersed in the anhydrous base to form a homogenous dispersion without any large aggregates or clumps of particles. In some embodiments, the topical administration of a homogenous dispersion of selenium disulfide in an anhydrous semi-solid base, as described herein, to the eyelid margin of a patient, for treating Demodex, does not cause any irritation to the eyes of the patient.

Chemical and Storage Stability of Selenium Disulfide Dispersion in Anhydrous Semi-Solid Ophthalmic Base Prior to the disclosures provided herein, surfactants and various suspending agents were required to stabilize selenium disulfide suspension in liquid and semi-solid dosage forms, and enable its topical application. The stable anhydrous selenium disulfide formulations described herein, in some embodiments, unexpectedly are stable without the use of surfactants or suspending agents or dispersing agents.

In some embodiments, the stable anhydrous selenium disulfide formulations described herein are physically stabilized against aggregation and chemically stabilized against degradation without the addition of surfactants, dispersing agents, or suspending agents.

In some embodiments, the stability of the formulations is tested under accelerated stability conditions, at a temperature between about of 40° C. and 60° C. for an extended storage period.

Stability of an ophthalmic formulation is determined by the extent of chemical degradation of the active ingredients via processes such as hydrolysis, oxidation, etc, during the period of storage.

Chemical Degradation is Characterized by Formation of Degradants

In some embodiments, the total amount of degradants in the stable anhydrous selenium disulfide formulations described herein does not increase over time during storage period. In some embodiments, the total amount of degradants in the stable anhydrous formulations described herein does not increase when the formulation is tested under accelerated stability conditions, at a temperature of about 40° C. and 60° C. and the degradation observed is lower in comparison to marketed $SeS_2$ drug products. Another embodiment provides the composition further comprising small amounts of degradants of selenium disulfide, and wherein the amount of the degradants does not increase above 1% of the total weight of the composition.

In some embodiments, the chemical stabilization of the stable anhydrous selenium disulfide formulations described herein is attributed to the reduced water content of the formulations. In some embodiments, the chemical stabilization of the stable anhydrous selenium disulfide formulations described herein is attributed to the anhydrous nature of the formulation.

In some embodiments, the chemical stabilization of the stable anhydrous selenium disulfide formulations described herein is attributed to the lack of polyoxyethylene comprising stabilizing emulsifiers and dispersing agents in the formulation In some embodiments, drug instability in pharmaceutical formulations is detected by a change in the physical appearance, color, odor, taste, or texture of the formulation. In some embodiments, the stable anhydrous selenium disulfide formulations described herein do not exhibit any substantial change in color during a period of storage, under elevated temperatures. In some embodiments, the period of storage is two weeks at a temperature of about 60° C.

Melting Point of Stable Anhydrous Selenium Disulfide Formulations

In some embodiments, the stable anhydrous selenium disulfide formulations described herein has a melting temperature between about 34° C. and about 50° C. In some embodiments, the stable anhydrous selenium disulfide formulations described herein has a melting temperature of about 34° C., about 35° C., about 36° C., about 37° C., about 38° C., about 39° C., about 40° C., about 41° C., about 42° C., about 43° C., about 44° C., about 45° C., about 46° C., about 47° C., about 48° C., about 49° C., or about 50° C. In some embodiments, the stable anhydrous selenium disulfide formulations described herein has a melting temperature close to and above the temperature of eyelid margin. In some embodiments, the melting point of the stable anhydrous selenium disulfide formulations described herein increases the bioavailability and efficacy of selenium disulfide.

Solid and Semi-Solid Dosage Form Composition Comprising Selenium Disulfide Dispersion in Anhydrous Semi-Solid Ophthalmic Base In some embodiments, the stable anhydrous selenium disulfide formulations described herein are part of a solid dosage form like a lip balm or a stick product, that is convenient to apply and spread over the eyelid margin in a similar manner to cosmetic eyelid product, whereas a very small amount of drug product is applied directly and precisely on the eyelid margin.

In some embodiments, the amount of drug product applied to the eyelid margin is about one mg. In other embodiments, the amount of drug product applied to the eyelid margin is less than 5 mg, less than 4 mg, less than 3 mg, or less than 2 mg.

In some embodiment, the stable anhydrous selenium disulfide composition comprises a synthetic or natural antioxidant selected from, for example, tocopherol or Vitamin E, EDTA (ethylenediamine tetraacetate), butylated hydroxyl anisole, butylated hydroxyl toluene, glutathione, astaxanthin, lutein, lycopene, propyl gallate, rosmarinic acid or ascorbyl palmitate.

In some embodiments, the stable anhydrous selenium disulfide formulations described herein are part of a semi-solid dosage form, such as an eye liner or an ointment product, that is convenient to apply and spread over the eyelid margin in a similar manner to cosmetic eyelid product, whereas a very small amount of drug product is applied directly and precisely on the eyelid margin.

Terms and Definitions

As used herein, the singular forms "a," "and," and "the" include plural referents unless the context clearly dictates otherwise. Thus, for example, reference to "an agent" includes a plurality of such agents, and reference to "the cell" includes reference to one or more cells (or to a plurality of cells) and equivalents thereof known to those skilled in the art, and so forth. When ranges are used herein for physical properties, such as molecular weight, or chemical properties, such as chemical formulae, all combinations and sub-combinations of ranges and specific embodiments therein are intended to be included. The term "about" when referring to a number or a numerical range means that the number or numerical range referred to is an approximation within experimental variability (or within statistical experimental error), and thus the number or numerical range may vary between 1% and 15% of the stated number or numerical range. The term "comprising" (and related terms such as "comprise" or "comprises" or "having" or "including") is not intended to exclude that in other certain embodiments, for example, an embodiment of any composition of matter, composition, method, or process, or the like, described herein, may "consist of" or "consist essentially of" the described features.

The term "Demodex" or "Demodex infestation" as used herein refers to the Demodex mite or the presence thereof. The Demodex infestation may be on and/or in an eye, tissue surrounding the eye (e.g., an eyelid, an eyelid margin, etc.) an orifice of the eyelid (e.g., follicle of an eyelash, meibomian gland, etc.), or any combination thereof. The Demodex mites may be, for example, Demodex *brevis* or Demodex folicularum. The Demodex infestation may comprise at least one mite, at least about 2 mites, at least about 5 mites, at least about 10 mites, at least about 50 mites, at least about 100 mites, at least about 500 mites, at least about 1,000 mites, at least about 5,000 mites, at least about 10,000 mites, or more. The Demodex mites may form colonies or clusters on and/or in an individual.

The term "ophthalmically-acceptable carrier" as used herein refers to a carrier that does not cause significant irritation to the eye of an organism when applied in accordance with the teachings of the present invention and does not abrogate the pharmacological activity and properties of an agent carried therewith.

Ophthalmically acceptable carriers are generally sterile, essentially free of foreign particles, and generally have a pH in the range of 5-8. Preferably, the pH is as close to the pH of tear fluid (7.4) as possible. Ophthalmically acceptable carriers are, for example, sterile isotonic solutions such as isotonic sodium chloride or boric acid solutions. Such carriers are typically aqueous solutions contain sodium chloride or boric acid. Also useful are phosphate buffered saline (PBS) solutions.

The term "ophthalmically safe" as used herein refers a pharmaceutical composition that is generally suitable and safe for direct placement on the eye without rinsing. An ophthalmically safe pharmaceutical composition typically has a tonicity and pH that is compatible with the eye and comprises materials, and amounts thereof, that are non-cytotoxic according to ISO (International Standards Organization) standards and U.S. FDA (Food and Drug Administration) regulations.

The pharmaceutical composition should be sterile in that the absence of microbial contaminants in the product prior to release should be statistically demonstrated to the degree necessary for such products. In some embodiments, the pharmaceutical composition described herein is "ophthalmically safe".

The term "effective amount" as used herein refers to the amount that is needed to achieve a particular condition, such as increasing lipid secretion from a meibomian gland, lowering the melting point of lipids secreted from a meibomian gland or reducing the viscosity of lipids secreted from a meibomian gland.

The term "therapeutically effective amount" as used herein refers to an amount of a therapeutically effective compound, or a pharmaceutically acceptable salt thereof, which is effective to treat, prevent, alleviate or ameliorate symptoms of a disease. The term "therapeutically effective compound" refers to a compound that is effective to treat, prevent, alleviate or ameliorate symptoms of a disease.

The term "substantially" or "substantial" as used herein generally refers to at least about 60% or 60%, about 70% or 70%, about 75% or 75%, about 80% or 80%, about 85% or 85%, about 90% or 90%, about 95% or 95%, about 96% or 96%, about 97% or 97%, about 98% or 98%, about 99% or 99% or higher relative to a reference such as, for example, the original composition or state of an entity. Thus, a composition that is "substantially-free" of surfactants indicates that at least about 60% or 60%, about 70% or 70%, or about 75% or 75%, about 85% or 80%, about 85% or 85%, about 90% or 90%, about 95% or 95%, about 96% or 96%, about 97% or 97%, about 98% or 98%, about 99% or 99% or higher amounts of surfactants have been removed from a composition.

"Pharmaceutically acceptable salt" includes both acid and base addition salts. A pharmaceutically acceptable salt of any one of the dual-acting Demodex pharmacological agents described herein is intended to encompass any and all pharmaceutically suitable salt forms. Preferred pharmaceutically acceptable salts of the compounds described herein are pharmaceutically acceptable acid addition salts and pharmaceutically acceptable base addition salts.

"Pharmaceutically acceptable acid addition salt" refers to those salts which retain the biological effectiveness and properties of the free bases, which are not biologically or otherwise undesirable, and which are formed with inorganic acids such as hydrochloric acid, hydrobromic acid, sulfuric acid, nitric acid, phosphoric acid, hydroiodic acid, hydrofluoric acid, phosphorous acid, and the like. Also included are salts that are formed with organic acids such as aliphatic mono- and dicarboxylic acids, phenyl-substituted alkanoic acids, hydroxy alkanoic acids, alkanedioic acids, aromatic acids, aliphatic and. aromatic sulfonic acids, etc. and include, for example, acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Exemplary salts thus include sulfates, pyrosulfates, bisulfates, sulfites, bisulfites, nitrates, phosphates, monohydrogenphosphates, dihydrogenphosphates, metaphosphates, pyrophosphates, chlorides, bromides, iodides, acetates, trifluoroacetates, propionates, caprylates, isobutyrates, oxalates, malonates, succinate suberates, sebacates, fumarates, maleates, mandelates, benzoates, chlorobenzoates, methylbenzoates, dinitrobenzoates, phthalates, benzenesulfonates, toluenesulfonates, phenylacetates, citrates, lactates, malates, tartrates, methanesulfonates, and the like. Also contemplated are salts of amino acids, such as arginates, gluconates, and galacturonates (see, for example, Berge S. M. et al., "Pharmaceutical Salts," *Journal of Pharmaceutical Science,* 66:1-19 (1997)). Acid addition salts of basic compounds are, in some embodiments, prepared by contacting the free base forms with a sufficient amount of the desired acid to produce the salt according to methods and techniques with which a skilled artisan is familiar.

"Pharmaceutically acceptable base addition salt" refers to those salts that retain the biological effectiveness and properties of the free acids, which are not biologically or otherwise undesirable. These salts are prepared from addition of an inorganic base or an organic base to the free acid. Pharmaceutically acceptable base addition salts are, in some embodiments, formed with metals or amines, such as alkali and alkaline earth metals or organic amines. Salts derived from inorganic bases include, but are not limited to, sodium, potassium, lithium, ammonium, calcium, magnesium, iron, zinc, copper, manganese, aluminum salts and the like. Salts derived from organic bases include, but are not limited to, salts of primary, secondary, and tertiary amines, substituted amines including naturally occurring substituted amines, cyclic amines and basic ion exchange resins, for example, isopropylamine, trimethylamine, diethylamine, triethylamine, tripropylamine, ethanolamine, diethanolamine, 2-dimethylaminoethanol, 2-diethylaminoethanol, dicyclohexylamine, lysine, arginine, histidine, caffeine, procaine, N,N-dibenzylethylenediamine, chloroprocaine, hydrabamine, choline, betaine, ethylenediamine, ethylenedianiline, N-methylglucamine, glucosamine, methylglucamine, theobromine, purines, piperazine, piperidine, N-ethylpiperidine, polyamine resins and the like. See Berge et al., *supra.*

The term "sulfhydryl group" as used herein refers to the —SH functional group.

The term "thiol group" as used herein refers to —C—SH or R—SH group, where R represents an alkane, alkene, or other carbon-containing group of atoms.

The term "disulfide" as used herein refers to a linked pair of sulfur atoms.

The term "disulfide bond" as used herein refers to a covalent bond, usually derived by the coupling of two thiol groups, the overall connectivity is therefore —S—S—. The linkage is also called an SS-bond or disulfide bridge.

The term "ophthalmically-acceptable excipient" as used herein refers to an excipient that does not cause significant irritation to the eye of an organism when applied in accordance with the teachings of the present invention and does not abrogate the pharmacological activity and properties of an agent carried therewith.

The term "keratolytic agent" and/or "keratoplastic agent" as used herein refers to an agent that softens, disrupts, dissolves, solubilizes, or loosens a keratinized obstruction, or prevents the formation of a keratinized obstruction. Specifically, the term "keratolytic agents" refers to agents used to promote softening and dissolution of keratin and the term "keratoplastic agents" refers to agents used to reduce keratin production.

The terms "treat," "treating," or "treatment" as used herein, include reducing, alleviating, abating, ameliorating, relieving, or lessening the symptoms associated with Demodex in either a chronic or acute therapeutic scenario. In one embodiment, treatment includes an increase in lipid production. In one embodiment, treatment includes an increase in lipid secretion. In one embodiment, treatment includes a decrease in the viscosity of the lipids secreted.

The term "recurrence," or "reducing relapse" refers to return of Demodex symptoms in a chronic therapeutic scenario.

The term "opening" refers to the clearing (at least in part) of an obstructed meibomian gland canal or orifice and/or maintaining the patency of the meibomian gland canal or orifice.

The term "dispersion" as used herein refers to a system in which particles are dispersed in a continuous phase of a different composition or state. The dispersions are solid dispersions.

The term "agglomerates", "aggregates", and "clumps of particles" as used herein refers to a collection of particles. The terms are intended to be synonymous to each other and are used interchangeably.

The term "anhydrous" as used herein refers to a composition containing less than 2% water by weight, or less than 1% water by weight, or a composition which does not contain any water.

The term "lipogenesis and lipid secretion enhancing selenium disulfide-containing (e.g., selenium disulfide ($SeS_2$)) drug or pharmaceutical agent" as used herein refer to a selenium disulfide-containing (e.g., selenium disulfide ($SeS_2$)) drug or pharmaceutical agent that causes increased differentiation of meibocytes or increases proliferation of meibocytes or increases the quantity of lipids secreted from the meibomian glands or alters the composition of meibum lipids.

The term "meibum lipids" as used herein refers to lipids secreted by meibomian gland.

The term "lotion" describes an emulsion liquid dosage form. This dosage form is generally for external application to the skin (US FDA Drug Nomenclature Monograph, number C-DRG-00201).

The term "cream" describes an emulsion semisolid dosage form, usually containing>20% water and volatiles and/or <50% hydrocarbons, waxes or polyols as the vehicle. A cream is more viscous than a lotion. This dosage form is generally for external application to the skin (US FDA Drug Nomenclature Monograph, number C-DRG-00201).

The term "ointment" describes a semisolid dosage form, usually containing<20% water and volatiles and/or >50% hydrocarbons, waxes or polyols as the vehicle. This dosage form is generally for external application to the skin or mucous membranes (US FDA Drug Nomenclature Monograph, number C-DRG-00201).

The term "solution" describes a clear, homogeneous liquid dosage form that contains one or more chemical substances dissolved in a solvent or mixture of mutually miscible solvents (US FDA Drug Nomenclature Monograph, number C-DRG-00201).

The term "suspension" refers to a heterogeneous mixture containing solid particles that are sufficiently large for sedimentation.

The term "lipid-derivative" as used herein generally refers to hydrophobic or amphiphilic molecules comprising at least one sulfhydryl group or at least one disulfide. The term "lipid-derivative" further refers to hydrophobic or amphiphilic molecules comprising at least one sulfhydryl group and at least one disulfide. The term "lipid-derivative" further refers to combinations and mixtures of lipid-derivatives.

The term "maintenance therapy" or "maintenance dosing regimen" refers to a treatment schedule for a subject or patient diagnosed with a disorder/disease, e.g., Demodex, to enable them to maintain their health in a given state, e.g., remission.

While preferred embodiments of the present disclosure have been shown and described herein, it will be obvious to those skilled in the art that such embodiments are provided by way of example only. Numerous variations, changes, and substitutions will now occur to those skilled in the art without departing from the disclosure. It should be understood that various alternatives to the embodiments of the disclosure described herein may be employed in practicing the disclosure.

EXAMPLES

Example 1—Pharmaceutical Compositions

A pharmaceutical composition comprising selenium disulfide is prepared that did not contain any surfactants, such as to avoid ocular hazards of surfactants, such as sodium lauryl sulfate (SLS). The composition is prepared by the combination of selenium disulfide ($SeS_2$) in combination with Petrolatum base (and in the absence of surface acting agents). Compositions comprising various concentrations of selenium disulfide are prepared, such as 0.1 wt. %, 0.5 wt. %, 1 wt. %, 1.5 wt. %, 2 wt. %, and 2.5 wt. %.

Various compositions prepared as described above are administered to the eye or eyelid (e.g., margin thereof) of albino rabbits. Various compositions are administered to distinct cohorts using various treatment protocols, such as based on frequency of administration (e.g., once daily, twice daily, every other day, and once weekly) and volume of administration (e.g., <25 μL, <25 μL or >25 μL per administration). Compositions lacking selenium disulfide are administered to a separate cohort to establish a control.

Example 2—Animal Safety

Albino rabbits are evaluated, and an accurate volume of the composition is ejected from a device (e.g., micropipette) and is delivered to the lower eyelid of the rabbits. In one example, the volume is ~25 μL (equivalent to 20 mg in weight). The rabbits are examined daily.

2.5% $SeS_2$ at a dosing volume of 25 μL is administered to the animals. Signs of conjunctival redness and corneal staining 48 hours after a single application (⅓ animals) is presented, and at day 7, after the second application, signs of conjuctival redness and corneal staining are presented in 3/3 animals (in a bi-weekly regimen or treatment). Corneal staining is presented in ⅚ animals during daily application from day 3, and keratitis is presented in all animals by day 7, including red and swollen eyelids. The vehicle alone did not demonstrate such effects in the animals.

This is a surprising finding because it is assumed that surfactant free $SeS_2$ formulation will resolve the occurrence of such reported adverse effect. Also, while previous reports on $SeS_2$ in surfactant-based formulations have an effect on the cornea, dermal studies have shown that following a single application, or after 13 weeks daily application, selenium disulfide (1%) did not appear to be irritant to rabbit dermis, beyond that seen with the shampoo vehicle (NDA 16-888).

Therefore, a reduced dose of 5 μL (equivalent to 4 mg) is placed on the lid of the rabbits. While this dose is documented to mix well with the tear film, resides on the surface of the lid, and mixes into the pre-corneal tear film covering the cornea, there is no evidence for any of the effects observed with any of the concentrations tested—the maximum concentration being 2.5%.

Example 3: Clinical Tolerance

Confirmation of the potential harmful effect of higher volume is demonstrated when a sliver of 25 μL (20 mg) of the composition containing 2.5% $SeS_2$ with petrolatum is placed on the lower eyelid of the right eye of a healthy male with no ocular history. About 4 hours later, pain is reported, and, upon clinical examination, keratitis is observed with multiple punctate over the center exposed part of the cornea. The eye is treated with lubricants and local NSAID, and the keratitis is resolved within 48 hours.

In summary, no clinical or microscopic findings are observed for any tested concentration, (i.e., 0.5%, 1.0% or 2.5%) or dosing regimen (i.e., twice weekly or once daily) with a clinical dose volume of 5 μL. Therefore, therapeutic concentration of $SeS_2$ are safely used on the eyelid margin as long as the dose volume is limited to below 25 μL, such as 5 μL, in volume.

A composition described herein, such as in Example 1, is administered to the inner surface of an eyelid identified as being pre-symptomatic or symptomatic for Demodex. After administration (e.g., single and/or multiple administration), the evaluation (e.g., symptoms and signs) described herein is re-administered to determine improvement in condition.

Example 4—Clinical Study

Three (3) groups of patients are given doses of 0.1%, 0.5%, and 1% of $SeS_2$ and a device to assist them to expel an exact (5 μL) volume of $SeS_2$ ointment onto an applicator or their finger. Patients apply the ointment either twice weekly or once daily for 3 months. Nine patients were randomized to group 1 (0.1%,) between Sep. 10, 2018 and Oct. 19, 2018.

Composition 0.1% dosed either twice-weekly or once-daily were considered safe and well tolerated by an independent Data Review Committee (DRC). Ten patients were randomized to Group 2 (0.5%) between Oct. 19, 2018 and Feb. 20, 2019. Composition 0.5% dosed either twice-weekly or once-daily were considered safe and well tolerated by an independent Data Review Committee (DRC). Nine patients were randomized to Group 3 (1%) between 13th of March 2019 and Jul. 29, 2019. Composition 1% dosed either twice-weekly or once-daily were considered safe and well tolerated by an independent Data Review Committee (DRC).

Example 5-Clinical Study

In a parallel to the study of Example 4, seven (7) healthy subjects the amount of drug actually applied over the eyelid was calculated by weighing the swab on which 4 mg of drug product was placed over before and after application. Each subject repeated the application 7 to 8 times. The average amount remaining on the lid (calculated as the difference between was applied on the swab and what remained on the swab after application) among all applications was 2.23 mg±0.91.

Example 6—Rabbit Study with 1 wt. % $SeS_2$ Concentration

In a study conducted on New-Zealand rabbits a concentration of 1 wt. % was used once daily for up to 8 days on 3 rabbits. A total dose of 4 mg was applied to the lower lid.

During the study period the following observations were made:

One (1) animal was squinting with no ophthalmic findings, one animal had corneal staining and a third animal had eyelid swelling Example 7-Rabbit Study with 0.5 wt. % to 2.5 wt. % $SeS_2$ Concentration On a subsequent study to Example 6, concentrations ranging from 0.5 wt. % to 2.5 wt. % were used on New-Zealand rabbits, once daily to twice weekly for 28 days. The dose was carefully applied to the lower eyelid with avoiding trapping of access drug in the lower fornix.

The ophthalmic observations made in the study which was about 4 times longer than the previous once described was that similar or higher concentrations which are given in controlled way were safer.

Example 8-Rabbit Study with 1 wt. % $SeS_2$ Concentration

In a parallel study to Examples 7, in which the method was used on rabbits, the amount of drug before and after application was calculated 5 times for 3 different technicians and the following measurements were recorded:

Technician #1: Mean 2.53 mg±0.74

Technician #2: Mean 2.18 mg±0.32

Technician #3: Mean 2.24 mg±0.38

Given that the particles of $SeS_2$ are dispersed within the ointment and do not diffuse through it similar to particles dissolved in a solution, dermal application such as on the eyelid imply that only those particles that are at the surface and are coming in contact with the skin are able to extract their activity on the target cells.

It is therefore important to be able to apply a thin layer that on the one hand cover the lid margin to allow drug activity while avoiding access that would create safety concerns.

Example 9-Application to a Lower Eyelid Margin

We conducted an experiment to determine the minimal amount that can be applied on the lid margin while making sure the lid margin is well covered. Two eyes were tested.

An analytical scale with a 0.1 mg accuracy was used. The scales were calibrated and the swab's weight was measured. A sliver of black pigmented petrolatum-based ointment was extracted out of a tube of which a small portion of was placed over the tip of the swab. The swab was then weighted again to determine the total weight of the drug product placed on the swab.

The subject then took the swab and use it to spread the ointment over the lower lid margin.

Figure 2:
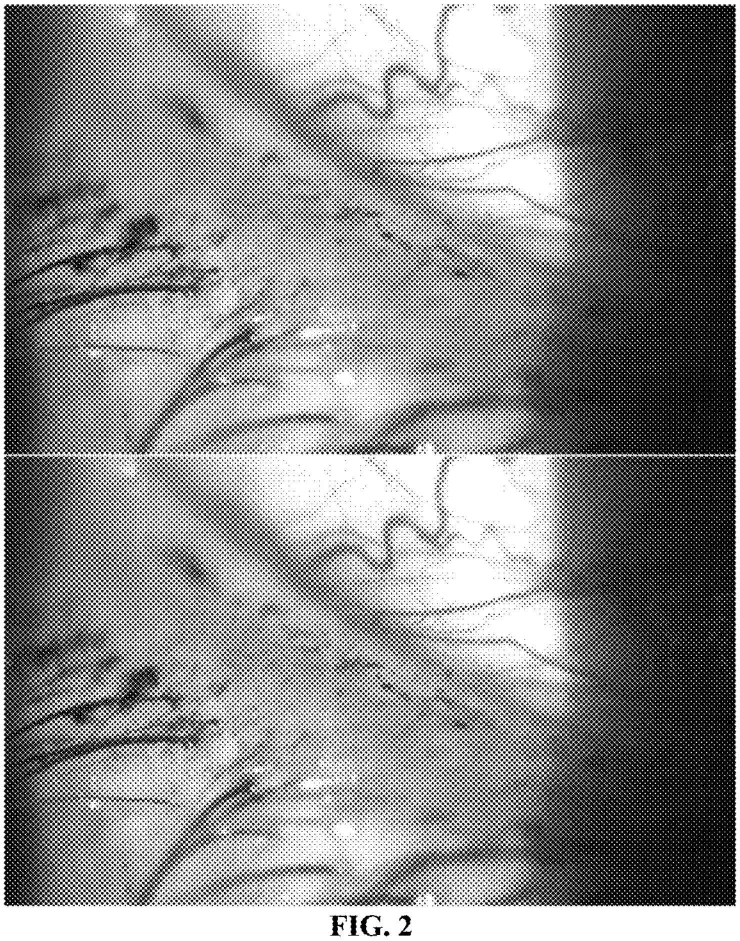
FIG. 2 is an image of a lower lid margin showing the uniform spread of a low volume (0.3 mg) petrolatum composition over the lid margin.
Figure 3:
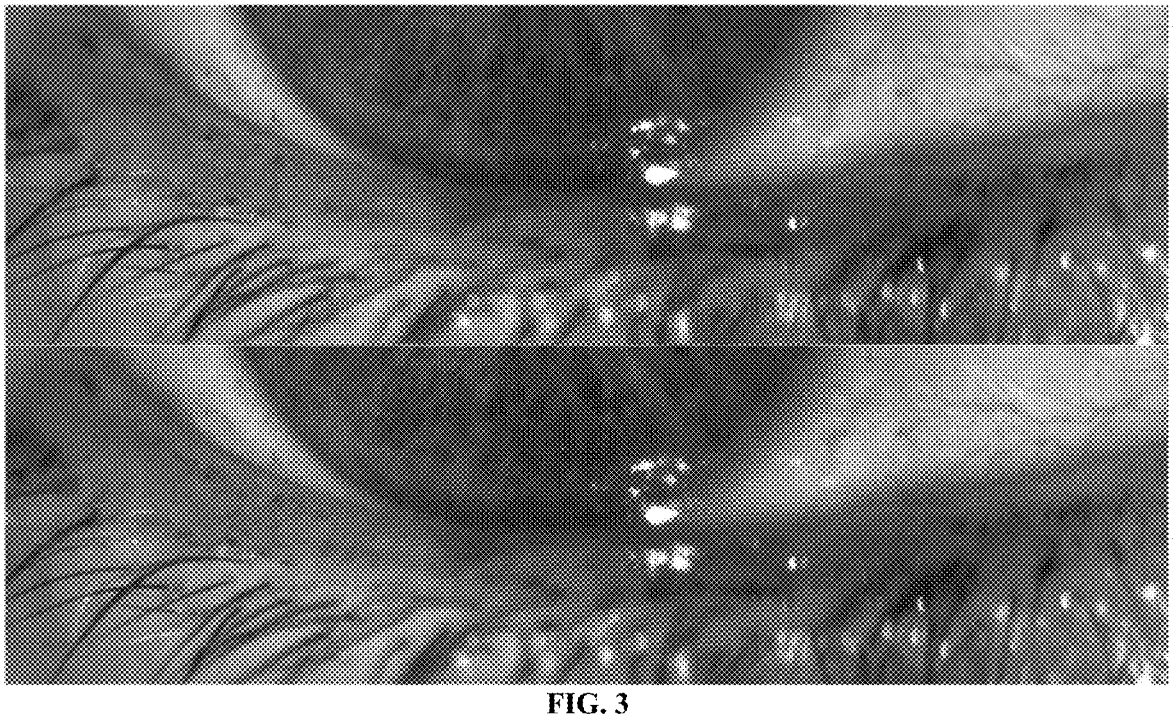
FIG. 3 is an image of a lower lid margin showing the uniform spread of another low volume (0.4 mg) of a petrolatum composition over the temporal, central and nasal areas of the lower lid margin.

The outcome was measured by calculation of the weight of drug product remaining on the lid margin and evaluation of the separability of the drug product over the entire lid margin The minimal dose that was sufficient to obtain full cover of the meibomian glands of the lower eyelid was 0.3 (~0.3 microliters) and 0.4 mg (~0.4 microliters) as can be seen in FIG. 2 and FIG. 3, respectively.

Example 9-Eyelash Study

Eyelid margin infestation with Demodex folliculorum mites is a known risk factor for Blepharitis. Historical off-label use of $SeS_2$ products to treat blepharitis and demodex blepharitis, suggest that $SeS_2$ may prove clinically useful in the eradication of Demodex blepharitis. In vitro assessment of the anti-demodectic properties of $SeS_2$ was aimed to serve as the first step towards this confirmation.

The study comprised of eyelashes from patients, 18 years old or older, with a history of Demodex blepharitis and positive Demodex folliculorum on eyelids, combined with presence of cylindrical dandruff (a pathognomonic finding of Demodex infestation in the eyelids), at the time of visit. The patients were recruited at the offices of Ophthalmic Consultants of Long Island (OCLI), in Long Island, N.Y., (Principal Investigators: Henry D. Perry, Jose Quintero).

Two different formulations of $SeS_2$ were tested: A. AZR-MD-001: a semi solid, ointment formulation contains $SeS_2$ as the active ingredient in Vaseline 100%, and b. A suspension of $SeS_2$ in Carboxymethyl Cellulose [CMC]). Each formulation was tested at four different concentrations (0.1%, 0.5%, 1%, 4%). Tea tree oil 100% served as a positive control for killing Demodex, while Balanced Salt Solution 0.9% [BSS] was used as a negative control. The vehicles of Azura's formulation, Vaseline 100% and CMC 1.5% were tested as well. Total of 6 groups were tested as described in Table no. 1

TABLE 1

| Group no. | Test item | concentrations |
|---|---|---|
| 1 | Vaseline | 100% |
| 2 | Carboxymethyl Cellulose (CMC) | 1.5% |
| 3 | SeS2 in Carboxymethyl Cellulose (CMC) | 0.1%, 0.5%, 1%, 4% |
| 4 | AZR-MD-001 | 0.1%, 0.5%, 1%, 4% |
| 5 | Tea Tree oil | 100% |
| 6 | Balanced Salt Solution (BSS) | 0.9% |

Viable Demodex folliculorum mites were retrieved from positive epilated eyelashes (one eyelash per eyelid) and the Demodex mites were counted using light microspore, and later randomly assigned to each of the different treatments.

Positive eyelashes were defined by rotary movements of the mites' legs as noted by direct microscopic viewing on a cytology glass slide.

Each treatment group consists on 5 eyelashes, with 3-5 mites/eyelash.

A 30 microliter volume of each of the test items was dispensed over the positive eyelashes, using a micropipette, to ensure complete coverage of the organism(s) with the selected test item. For the semi-solid drug test items, a length of 20 mm (equal to a 30 microliters in weight) was dispensed using a ruler.

Viability assessment commences on application of the treatment and every 5 minutes for a duration of 30 seconds, and until cessation of rotary movement for up to 150-minute time interval has passed. Since an eyelash can contain up to 6 organisms, the investigator noted the time, behavior and cessation, when applicable, of each of the demodex presence on the lash.

The results of the study are summarized in Table 2.

The validity of the test system was proved by the expected results of the negative [BSS] and positive control [Tea Tree oil]: no effect on Demodex killing by the BSS, while 100% death (11/11) by the positive control.

The vehicles of Azura's formulations, Vaseline 100% and CMC 1.5% had no effect on Demodex killing nor on the clinical behavior of the mites.

A highly unique, unexpected phenomenon of mites leaving the eyelashes and moving away from the eyelash towards the surface, following the treatment with $SeS_2$, was observed for all Azura's $SeS_2$ based formulations (Vaseline and CMC based) and at all concentrations (0.1%, 0.5%, 1%, 4%).

No killing effect of $SeS_2$ were observed for $SeS_2$ 0.1%, 0.5% and 100 in neither CMC or Vaseline; however at the highest concentration of 40%, $SeS_2$ in both Vaseline and CMC, caused death of the Demodex mites, at rates of 10% and ~36.4%, respectively.

TABLE 2

| Group | Test Item | Concentration | Description | No. of Demodex tested | No. of Demodex killed [by 150 min] | Demodex Behavior |
|---|---|---|---|---|---|---|
| 1 | Vaseline | 100% | Vehicle of ointment | 14 | 0 | No effect |
| 2 | CMC | 1.5% | Vehicle | 12 | 0 | No effect |
| 3 | $SeS_2$ [in CMC] | 0.1% | Active | 8 | 0 | Demodex mites moved away from the eyelash |
| | | 0.5% | Active | 13 | 0 | |
| | | 1% | Active | 10 | 0 | |
| | | 4% | Active | 11 | 4 [36.4%], <40 min | |
| 4 | $SeS_2$ ointment | 0.1% | Active | 12 | 0 | Demodex mites moved away from the eyelash |
| | | 0.5% | Active | 9 | 0 | |
| | | 1% | Active | 13 | 0 | |
| | | 4% | Active | 10 | 1 [10%], By 75 min | |
| 5 | Tea Tree Oil | 100% | Positive Control | 11 | 11 [100%], by 25 min | No effect |
| 6 | Balanced Salt Solution (BSS) | 0.9% | Negative Control | 10 | 0 | No effect |

The anti-Demodectic properties of $SeS_2$ were confirmed in this in vitro study.

$SeS_2$ 4% caused death of the mites. The death rate was higher for a CMC vehicle than of a Vaseline vehicle. The difference can be explained by two factors; 1. a higher exposure of the mites to the API when is in a suspension rather than in thick Vaseline, 2. the Vaseline itself hardened the observation of the mites due to its thick nature, which have led to a lower visibility of the mites.

The most interesting, unexpected observation for $SeS_2$ was that of mites leaving the eyelashes and moving away from the eyelash, suggesting of repellent properties of Selenium Disulfide against Demodex. The repellency was observed for all $SeS_2$ formulations and even at low concentrations of Selenium Disulfide is highly suggestive that $SeS_2$ may be effective clinically in cases of Demodex Blepharitis, by repelling the mites and causing them to move away from the eyelashes back to their origin in the skin of the face. It is highly possible that $SeS_2$ might also prevent the migration of Demodex onto the eyelashes from the first place. Killing the mites may therefore not be necessary for clinically positive results. As disclosed herein, $SeS_2$ has been reported to repel mites and thus represents a novel application. At effective concentrations for repelling mites, $SeS_2$ is both non-toxic to people and the environment.

What is claimed is:

1. A method for treating Demodex or an infiltration thereof in or around an eye of an individual in need thereof, the method comprising:

providing a therapeutically effective amount of a pharmaceutically composition; and administering the therapeutically effective amount of the pharmaceutical composition to an eyelid of the individual;

the pharmaceutical composition comprising the therapeutically effective amount of $SeS_2$ in a therapeutically effective concentration, the therapeutically effective concentration being about 0.05 wt. % to about 3 wt. % of $SeS_2$; and the pharmaceutical composition being delivered to the eyelid in a volume of at most about 5 microliters (μL).

2. The method of claim 1, the therapeutically effective concentration of $SeS_2$ is sufficient to reduce a population of Demodex, inhibit an overgrowth of Demodex, or a combination thereof on the eyelid of the individual.

3. The method of claim 1, wherein the therapeutically effective concentration of $SeS_2$ is about 0.5 wt. % to about 1.0 wt. %.

4. The method of claim 1, wherein the pharmaceutical composition is in the form of an ointment, the ointment comprising petrolatum.

5. The method of claim 1, further comprising dispensing about 15 μL or less of the pharmaceutical composition from a device that is configured to provide a dispensed volume of about 15 μL or less.

6. The method of claim 1, wherein the pharmaceutical composition is administered by the individual.

7. The method of claim 1, wherein the pharmaceutical composition consists essentially of the therapeutically effective amount of selenium disulfide ($SeS_2$) and an oleaginous base.

8. The method of claim 7, wherein the oleaginous base comprises petrolatum.

9. The method of claim 7, wherein the oleaginous base is petrolatum.

10. The method of claim 3, wherein the therapeutically effective concentration of $SeS_2$ is about 0.5 wt. %.

11. The method of claim 10, wherein the pharmaceutical composition is delivered to an eyelid margin of the eyelid of the individual.

12. The method of claim 9, wherein the therapeutically effective concentration of $SeS_2$ is about 0.5 wt. %.

13. The method of claim 9, wherein the pharmaceutical composition is delivered to an eyelid margin of the eyelid of the individual.

14. The method of claim 12, wherein the pharmaceutical composition is delivered to an eyelid margin of the eyelid of the individual.

* * * * *